United States Patent
Burkholz et al.

(10) Patent No.: US 10,984,910 B2
(45) Date of Patent: *Apr. 20, 2021

(54) SYSTEM AND METHOD FOR ASSURING PATIENT MEDICATION AND FLUID DELIVERY AT THE CLINICAL POINT OF USE

(71) Applicant: Becton, Dickinson and Company, Franklin Lakes, NJ (US)

(72) Inventors: Jonathan Karl Burkholz, Salt Lake City, UT (US); Jeff O'Bryan, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 170 days.

This patent is subject to a terminal disclaimer.

(21) Appl. No.: 16/223,321

(22) Filed: Dec. 18, 2018

(65) Prior Publication Data

US 2019/0117888 A1   Apr. 25, 2019

Related U.S. Application Data

(63) Continuation of application No. 14/608,424, filed on Jan. 29, 2015, now Pat. No. 10,188,791.
(Continued)

(51) Int. Cl.
*G16H 40/67* (2018.01)
*G16H 20/17* (2018.01)
(Continued)

(52) U.S. Cl.
CPC ......... *G16H 40/67* (2018.01); *A61B 5/15003* (2013.01); *A61B 5/154* (2013.01);
(Continued)

(58) Field of Classification Search
CPC ............... A61M 5/16831; A61M 5/14; A61M 5/31525; A61M 5/427; A61M 5/142;
(Continued)

(56) References Cited

U.S. PATENT DOCUMENTS 6,775,409 B1   8/2004   Brunelli et al.
8,531,517 B2   9/2013   Tao
(Continued)

FOREIGN PATENT DOCUMENTS

EP   1944733 A2   7/2008
EP   2816358 A1   12/2014
(Continued)

OTHER PUBLICATIONS

Poon et al., "Effect of Bar-Code Technology on the Safety of Medication Administration", The New England Journal of Medicine, 2010, pp. 1698-1707, vol. 362:18.

*Primary Examiner* — Bhisma Mehta
*Assistant Examiner* — James D Ponton
(74) *Attorney, Agent, or Firm* — The Webb Law Firm

(57) ABSTRACT

A system for confirmation of fluid delivery to a patient at the clinical point of use is provided. The system includes a wearable electronic device. The wearable electronic device has a housing; at least one imaging sensor associated with the housing; a data transmission interface; a data reporting accessory for providing data to the user; a microprocessor for managing the at least one imaging sensor, the data transmission interface, and the data reporting accessory; and a program for acquiring and processing images from the at least one imaging sensor. The system further includes a fluid delivery apparatus; and one or more identification tags attached to or integrally formed with the fluid delivery apparatus. The program processes an image captured by the at least one imaging sensor to identify the one or more (Continued)

identification tags and acquires fluid delivery apparatus information from the one or more identification tags.

18 Claims, 11 Drawing Sheets

Related U.S. Application Data

(60) Provisional application No. 61/933,024, filed on Jan. 29, 2014.

(51) Int. Cl.

| | | |
|---|---|---|
| A61M 5/315 | (2006.01) | |
| A61M 5/42 | (2006.01) | |
| G16H 10/60 | (2018.01) | |
| A61M 5/14 | (2006.01) | |
| A61B 5/15 | (2006.01) | |
| A61B 5/154 | (2006.01) | |
| G16H 10/40 | (2018.01) | |
| G16H 40/63 | (2018.01) | |
| G06K 9/00 | (2006.01) | |
| G16H 30/20 | (2018.01) | |
| A61M 5/142 | (2006.01) | |
| A61M 5/168 | (2006.01) | |
| A61M 5/172 | (2006.01) | |
| A61B 5/157 | (2006.01) | |
| A61B 10/00 | (2006.01) | |
| A61B 10/02 | (2006.01) | |
| H04N 5/225 | (2006.01) | |
| H04N 5/44 | (2011.01) | |
| H04N 7/18 | (2006.01) | |
| G06F 19/00 | (2018.01) | |
| A61B 90/96 | (2016.01) | |
| A61B 90/90 | (2016.01) | |
| A61M 5/20 | (2006.01) | |
| A61M 5/28 | (2006.01) | |
| A61M 5/145 | (2006.01) | |
| A61M 5/158 | (2006.01) | |
| G16H 30/40 | (2018.01) | |
| G16H 10/65 | (2018.01) | |

(52) U.S. Cl.
CPC ........ *A61B 5/157* (2013.01); *A61B 5/150748* (2013.01); *A61B 5/150786* (2013.01); *A61B 5/150992* (2013.01); *A61B 10/0096* (2013.01); *A61B 10/02* (2013.01); *A61M 5/14* (2013.01); *A61M 5/142* (2013.01); *A61M 5/16831* (2013.01); *A61M 5/172* (2013.01); *A61M 5/315* (2013.01); *A61M 5/31525* (2013.01); *A61M 5/427* (2013.01); *G06F 19/00* (2013.01); *G06K 9/00771* (2013.01); *G16H 10/40* (2018.01); *G16H 10/60* (2018.01); *G16H 20/17* (2018.01); *G16H 30/20* (2018.01); *G16H 40/63* (2018.01); *H04N 5/2252* (2013.01); *H04N 5/44* (2013.01); *H04N 7/18* (2013.01); *A61B 5/150732* (2013.01); *A61B 5/150847* (2013.01); *A61B 90/90* (2016.02); *A61B 90/96* (2016.02); *A61M 5/1452* (2013.01); *A61M 5/20* (2013.01); *A61M 5/28* (2013.01); *A61M 2005/1588* (2013.01); *A61M 2205/3306* (2013.01); *A61M 2205/3389* (2013.01); *A61M 2205/3561* (2013.01); *A61M 2205/3569* (2013.01); *A61M 2205/3576* (2013.01); *A61M 2205/52* (2013.01); *A61M 2205/583* (2013.01); *A61M 2205/6009* (2013.01); *A61M 2205/6054* (2013.01); *A61M 2205/6063* (2013.01); *A61M 2205/6072* (2013.01); *G06K 2209/05* (2013.01); *G16H 10/65* (2018.01); *G16H 30/40* (2018.01)

(58) Field of Classification Search
CPC ........ A61M 5/172; A61M 5/315; A61M 5/20; A61M 5/28; A61M 5/1452; A61M 2005/1588; A61M 2205/3389; A61M 2205/3561; A61M 2205/3569; A61M 2205/52; A61M 2205/6009; A61M 2205/6054; A61M 2205/6063; A61M 2205/6072; A61M 2205/3306; A61M 2205/3576; A61M 2205/583; G16H 40/63; G16H 30/40; G16H 30/20; G16H 20/17; G16H 10/60; G16H 10/40; G06K 9/00771; G06K 2209/05; G06K 9/36; G06K 9/46; G06K 9/4604; G06K 9/58; G06K 9/60; G06K 9/62; G06K 9/74; G06K 9/78; G06K 9/80; G06F 19/3468; G06F 19/00; G06F 19/3418; H04N 5/2252; H04N 5/44; H04N 7/18; G06Q 50/24; G06Q 50/22; G06T 7/0012; G06T 7/0014; G06T 7/0016; A61B 5/15003; A61B 5/150748; A61B 5/150786; A61B 5/154; A61B 5/150992; A61B 5/157; A61B 10/0096; A61B 10/02; A61B 5/150732; A61B 5/150847; A61B 90/96; A61B 90/90

See application file for complete search history.

(56) References Cited

U.S. PATENT DOCUMENTS

| | | |
|---|---|---|
| 2001/0056258 A1 | 12/2001 | Evans |
| 2003/0135388 A1 | 7/2003 | Martucci et al. |
| 2005/0236488 A1 | 10/2005 | Kricorissian |
| 2006/0178578 A1 | 8/2006 | Tribble et al. |
| 2007/0148046 A1 | 6/2007 | Nakaya |
| 2007/0161909 A1* | 7/2007 | Goldman ............ A61B 5/0059 600/476 |
| 2008/0194930 A1* | 8/2008 | Harris ................ A61B 90/36 600/310 |
| 2009/0318791 A1 | 12/2009 | Kaastrup |
| 2010/0217623 A1* | 8/2010 | Schoenberg ........... G06Q 50/22 705/3 |
| 2011/0251579 A1 | 10/2011 | Aklog et al. |
| 2012/0238851 A1 | 9/2012 | Kamen et al. |
| 2013/0172093 A1 | 7/2013 | Leech |
| 2013/0204227 A1 | 8/2013 | Bochenko et al. |
| 2014/0184422 A1 | 7/2014 | Mensinger et al. |
| 2014/0188076 A1 | 7/2014 | Kamen et al. |
| 2014/0331157 A1 | 11/2014 | Yoshigahara et al. |
| 2015/0120321 A1 | 4/2015 | David et al. |

FOREIGN PATENT DOCUMENTS

| | | |
|---|---|---|
| JP | 2006500077 A | 1/2006 |
| JP | 2006068224 A | 3/2006 |
| JP | 2007178251 A | 7/2007 |
| JP | 2007535979 A | 12/2007 |
| JP | 201187678 A | 5/2011 |
| JP | 201322098 A | 2/2013 |
| JP | 201322099 A | 4/2013 |
| JP | 2013114315 A | 6/2013 |
| WO | 2013122013 A1 | 8/2013 |

\* cited by examiner

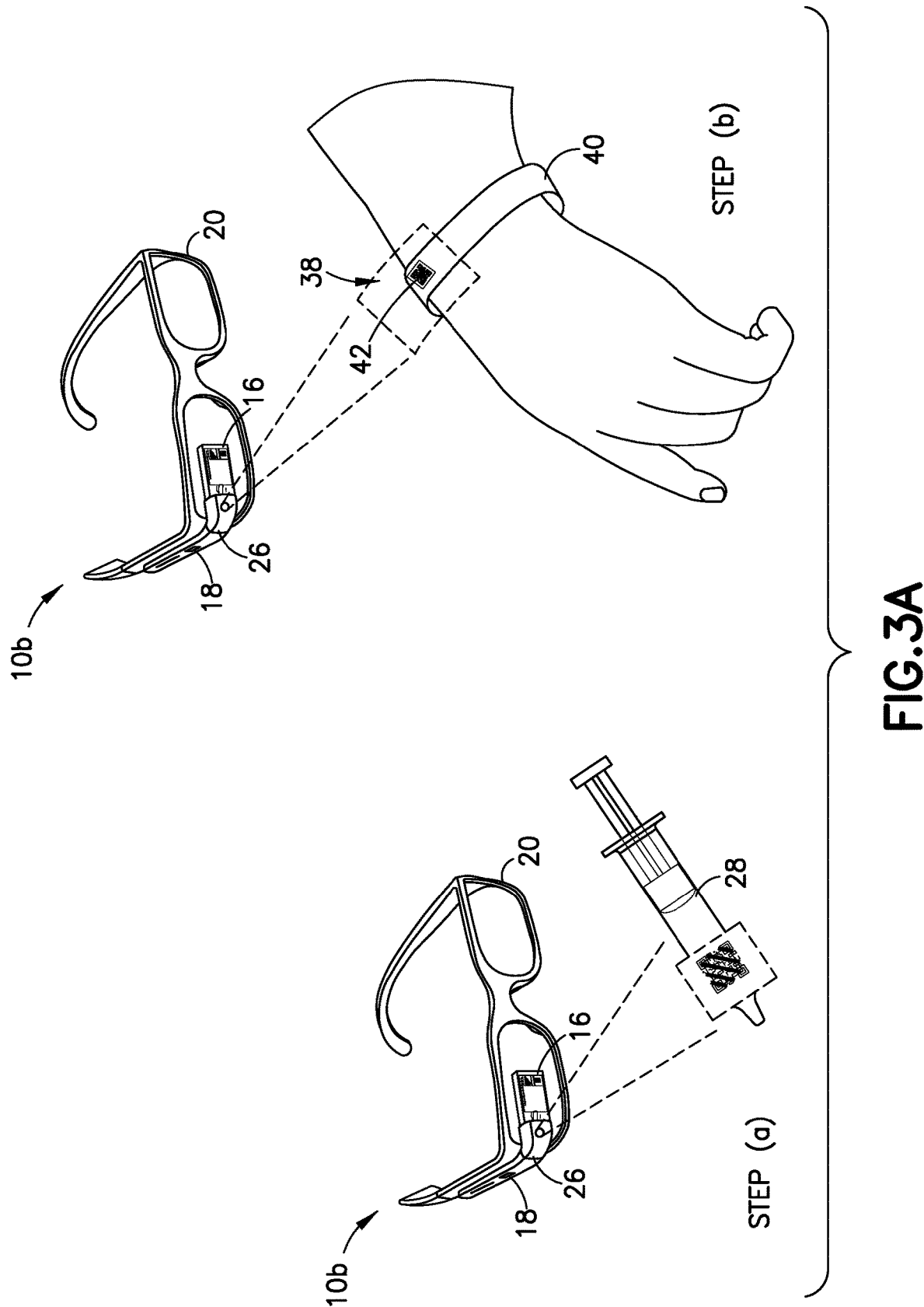

SYSTEM AND METHOD FOR ASSURING PATIENT MEDICATION AND FLUID DELIVERY AT THE CLINICAL POINT OF USE

CROSS-REFERENCE TO RELATED APPLICATION

The present application is a continuation of U.S. patent application Ser. No. 14/608,424 entitled "System and Method for Assuring Patient Medication and Fluid Delivery at the Clinical Point of Use" filed Jan. 29, 2015, which issued as U.S. Pat. No. 10,188,791 on Jan. 29, 2019, and which claims priority to U.S. Provisional Application No. 61/933,024 entitled "System and Method for Assuring Patient Medication and Fluid Delivery at the Clinical Point of Use" filed Jan. 29, 2014, the entire disclosures of each of which are hereby incorporated by reference in their entirety.

BACKGROUND OF THE INVENTION

Field of the Invention

The present invention relates to systems and methods for identifying, confirming, and documenting delivery of medication and fluids to a patient, and, more particularly, to systems and methods that operate in a hands-free manner using a wearable electronic device.

Description of Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples may be analyzed to obtain medically useful information including chemical composition, hematology, coagulation, etc.

Similarly, fluid delivery to a patient is accomplished using a variety of vascular access devices, including syringes, auto-injectors, pen injectors, catheters, and infusion devices. In medical settings, a clinician or technician performs an injection by inserting a needle into a patient's vein. A therapeutic agent is directly or passively provided to the patient through the needle. For example, the medical technician may inject fluid by pressing a piston rod and plunger through a syringe barrel to expel fluid therefrom. Alternatively, a therapeutic agent may be provided passively from an IV bag through an infusion set.

Prior to performing a fluid sampling or fluid delivery procedure, the clinician or technician is responsible for obtaining any needed medical instruments and devices. The clinician or technician may also be responsible for performing an initial examination of the patient by checking temperature, heart rate, or breathing. The clinician or technician may review notes in the patient's medical chart or other printed instructions to ensure that these initial steps are performed correctly and that any necessary equipment has been obtained. Alternatively, the technician may scan bar codes or other identifying indicia on the obtained equipment to document that certain items are being used. The medical professional then obtains the fluid sample or performs the fluid injection. After the sample is collected or fluid injected, the clinician or technician may be required to provide appropriate documentation that the procedure has been completed. For example, the clinician or technician may write notes in a patient's medical chart, including the time the procedure was completed, a description of the procedure that was performed, and notes concerning any abnormal or unexpected occurrences. Furthermore, in the case of obtaining fluid samples, the medical professional may be responsible for closing or sealing the collected sample with tamperproof seals to prevent the sample from being compromised prior to testing. The technician or clinician may be responsible for verifying the seal by, for example, signing his or her name or initials on a breakable label covering the seal.

In many medical facilities, these preparation, confirmation, and documentation activities are performed manually by the clinician or technician either as the medical procedure is being performed or after the procedure is completed. For example, the clinician or technician may be responsible for manually labeling each collected fluid sample with identifying information about the patient before transferring the sample for testing. Similarly, the clinician or technician may be responsible for manually documenting the type of fluid injected to a patient in the patient's chart. The medical professional may also be expected to document the date and time that the procedure was performed. In some circumstances, the clinician or technician is provided with electronic documenting means, such as a computer, laptop computer, table PC, smart phone, or similar easily transportable computing device. However, the technician or clinician is still responsible for manually entering information to the electronic device. Alternatively, data entry technicians may be responsible for electronically entering information about the procedure that was performed based on notes taken by the clinician or technician. Furthermore, many larger medical facilities rely on electronic patient databases for electronically storing patient information. However, even such electronic databases still require manual entry of data either by the clinician or technician, or later data entry based on contemporaneous notes taken by the clinician or technician.

The numerous manual steps required before, during, and after fluid sampling or fluid delivery procedures introduce opportunities for user error. User errors may lead to incomplete or incorrect procedures being performed or may result in lost patient data. For example, the clinician or technician may inject an incorrect fluid volume, incorrect fluid type or concentration, or may not obtain a sufficient volume of fluid sample for the tests being performed. The medical clinician or technician may also forget to correctly document that a fluid sample was obtained or under what conditions the sample was obtained. Furthermore, the clinician or technician may fail to correctly record which patient provided a particular fluid sample. These problems may harm the patient or, at minimum, may require that certain fluid sample procedures must be repeated. Therefore, there is a need for a system for fluid delivery to a patient and a system for acquiring a test specimen that assists the clinician or technician in performing and documenting the medical procedure. The system should be configured to prevent errors that commonly occur during such procedures and should provide visual or auditory alerts when a mistake is made. The system should also be automatically integrated with existing patient data systems so that information about the type of procedure to perform is easily accessible to the clinician or technician. Additionally, confirmation that a procedure was performed and relevant information about the procedure may be automatically and directly provided to a patient's medical record to ensure that patient data is not lost. The systems and methods described hereinafter are provided to address some or all of these issues.

SUMMARY OF THE INVENTION

The system and method provided herein reduces the risk of medication infusion and delivery error and improves clinical workflow for identifying, confirming, and documenting fluid delivery of medication and fluids to a patient. These identification, confirmation, and documentation activities are accomplished in real-time and at the clinical point of use.

In accordance with an embodiment of the present invention, a system includes a wearable electronic device configured to be worn by a user. The wearable electronic device includes a housing, at least one imaging sensor associated with the housing, a data transmission interface for sending data to or receiving data from an external electronic device, and a data reporting accessory for providing data to the user. The wearable electronic device also includes a microprocessor for managing the at least one imaging sensor, the data transmission interface, and the data reporting accessory, and a program for acquiring and processing images from the at least one imaging sensor. The system further includes a fluid delivery apparatus for passively or actively delivering a therapeutic agent to a patient, and one or more identification tags attached to or integrally formed with the fluid delivery apparatus. The program processes an image captured by the at least one imaging sensor to identify the one or more identification tags and acquires fluid delivery apparatus information from the one or more identification tags.

In certain configurations, the program confirms completion of the fluid delivery procedure by processing an image acquired by the at least one imaging sensor. The program may report the fluid delivery apparatus information and a confirmation of completion of the fluid delivery procedure to the user via the data reporting accessory or transmit the information and the confirmation to the external electronic device via the data transmission interface.

The program may acquire and process images automatically to acquire information from the one or more identification tags and to confirm completion of the fluid delivery procedure. In certain configurations, the data reporting accessory provides information to the user in a hands-free manner.

The wearable electronic device may be a head-worn computer, and the data reporting accessory may be a projection prism configured to project a virtual layer to a field of view of the user. The virtual layer may include a user interface including a patient information portion, a dose confirmation portion, an identification tag confirmation portion, a fluid delivery apparatus volume indicator, or any combination thereof. The at least one imaging sensor may be a digital camera or digital video camera.

Optionally, the program may confirm completion of the fluid delivery procedure by processing a series of images of the fluid delivery apparatus acquired by the at least one imaging sensor to track movement of a movable portion of the fluid delivery apparatus from an initial position to a final position. The movable portion of the fluid delivery apparatus may be a plunger or piston rod movable through a body of the fluid delivery apparatus. The movable portion may be coated with a substance that enhances the visibility of the movable portion in the series of images captured by the at least one imaging sensor to improve the tracking of the movement of the movable portion.

In certain configurations, the fluid delivery apparatus may include one or more sensors configured to determine when a portion of the fluid delivery apparatus is inserted into a patient or to determine when fluid is expelled from the fluid delivery apparatus. The one or more sensors are directly or indirectly connected to the wearable electronic device, and data collected by the one or more sensors may be provided to the user via the data reporting accessory or transmitted to the external electronic device via the data transmission interface.

The wearable electronic device may further include a data storage medium for storing the program, the fluid delivery apparatus information, the confirmation of completion of the fluid delivery procedure, or images captured by the at least one imaging sensor. The wearable electronic device may also include a peripheral data entry device that allows the user to manually enter data to the wearable electronic device. The peripheral data entry device can be a motion sensor, gyroscope, pressure sensor, accelerometer, touchpad, touchscreen, or any combination thereof. The wearable electronic device can further include a power supply within the housing of the wearable electronic device. The data transmission interface may be configured to send data to and receive data from a patient data system.

Optionally, information received from the patient data system may include information about the procedure to be performed, information about the fluid delivery apparatus required for the procedure, or information about the patient. Information transmitted to the external electronic device can include the confirmation of completion of the fluid delivery procedure, a time and date of the procedure, a fluid injection volume of the procedure, a quality or type of fluid injected during the procedure, or any combination thereof. The fluid delivery apparatus may be one or more of a pre-filled syringe, a pen injector, an auto-injector, an infusion set, a catheter, a vascular access device, or any combination thereof.

The one or more identification tags may include a two-dimensional bar code, a three-dimensional bar code, a near field communication device, or a label having text readable by an optical character recognition algorithm. The program identifies the one or more identification tags in the image captured by processing the image to locate a positional marker on the fluid delivery apparatus and then locating the one or more identification tags based on the location on the image of the positional marker. The system may also include a patient identification device including or associated with identifying information about the patient, the patient identification device being readable by the at least one imaging sensor of the wearable electronic device.

In accordance with a further embodiment of the present invention, a system includes a wearable electronic device configured to be worn by a user. The wearable electronic device includes a housing, at least one sensor associated with the housing, a data transmission interface for sending data to or receiving data from an external electronic device, and a data reporting accessory for providing information to a user. The wearable electronic device also includes a microprocessor for managing the at least one sensor, the data transmission interface, and the data reporting accessory, and a program for acquiring and processing data acquired by the at least one sensor. The system further includes a fluid delivery apparatus for passively or actively delivering a therapeutic agent to a patient, one or more identification tags attached to or integrally formed with the fluid delivery apparatus, and a patient identification device including or associated with identifying information about the patient and readable by the at least one sensor.

In certain configurations, the program manages acquiring information from the one or more identification tags and patient identification device. The program may also determine whether the fluid delivery apparatus is sufficient for a fluid delivery procedure based on information acquired from the one or more identification tags and patient identification device.

The data reporting accessory can provide an alert to the user if the fluid delivery apparatus is not sufficient for the fluid delivery procedure. In certain configurations, the patient identification device includes locating circuitry for determining a location of the patient.

In accordance with another embodiment of the present invention a system includes a wearable electronic device configured to be worn by a user. The wearable electronic device includes a housing, at least one imaging sensor enclosed within or associated with the housing, a data transmission interface for sending data to or receiving data from an external electronic device, and a data reporting accessory for providing information to the user. The wearable electronic device also includes a microprocessor for managing the at least one imaging sensor, the data transmission interface, and the data reporting accessory, and a program for acquiring and processing images acquired by the at least one imaging sensor. The system further includes an infusion set for delivering one or more therapeutic agents from a fluid container to a patient via a vascular access device. The program determines a fluid flow rate for fluid being expelled from the fluid container by processing a series of images captured by the at least one imaging sensor to determine fluid flow from the fluid container.

The program may verify that the infusion set is correctly connected by identifying connection points between portions of the infusion set on an image of the infusion set captured by the at least one imaging sensor and processes a portion of the image including the connection points to determine whether a sufficient connection exists. The data reporting accessory may also alert the user when the program determines that a connection is not sufficient.

In accordance with still a further embodiment of the present invention a method for confirming fluid delivery to a patient at a clinical point of use includes the steps of actuating a fluid delivery apparatus by advancing a movable portion of the fluid delivery apparatus through a body of the fluid delivery apparatus to expel fluid therefrom, and acquiring a series of images of the fluid delivery apparatus, as the movable portion is being advanced through the body, with a wearable electronic device having at least one imaging sensor. The method also includes the steps of processing the series of images in real time to determine if the movable portion of the fluid delivery apparatus has advanced to an end-of-use position, and informing a user wearing the wearable electronic device that the fluid delivery is complete when an image showing the movable portion of the fluid delivery apparatus in the end-of-use position is acquired. The processing is performed automatically and without an actuation activity by the user.

Processing the series of images may be performed using a computer of the wearable electronic device, a virtual computer, an external dedicated electronic device wired or wirelessly connected to the wearable electronic device, or an external computer connected to the wearable electronic device via a data transmission interface. The method may also include processing at least one of the series of images to identify and extract information about the fluid delivery apparatus from an identification tag affixed to or integrally formed with the fluid delivery apparatus. In certain configurations, the fluid delivery apparatus is a syringe and the movable portion is a plunger that is advanced through a body of the syringe from an initial position at a proximal end of the body to the end-of-use position at a distal end of the body.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

FIG. 3A is a schematic representation of a hands-free system for assuring patient medication and fluid delivery having a wearable electronic device in the form of glasses and a patient identification device, according to the principles of the invention.

DETAILED DESCRIPTION OF THE PREFERRED EMBODIMENTS

Figure 1:
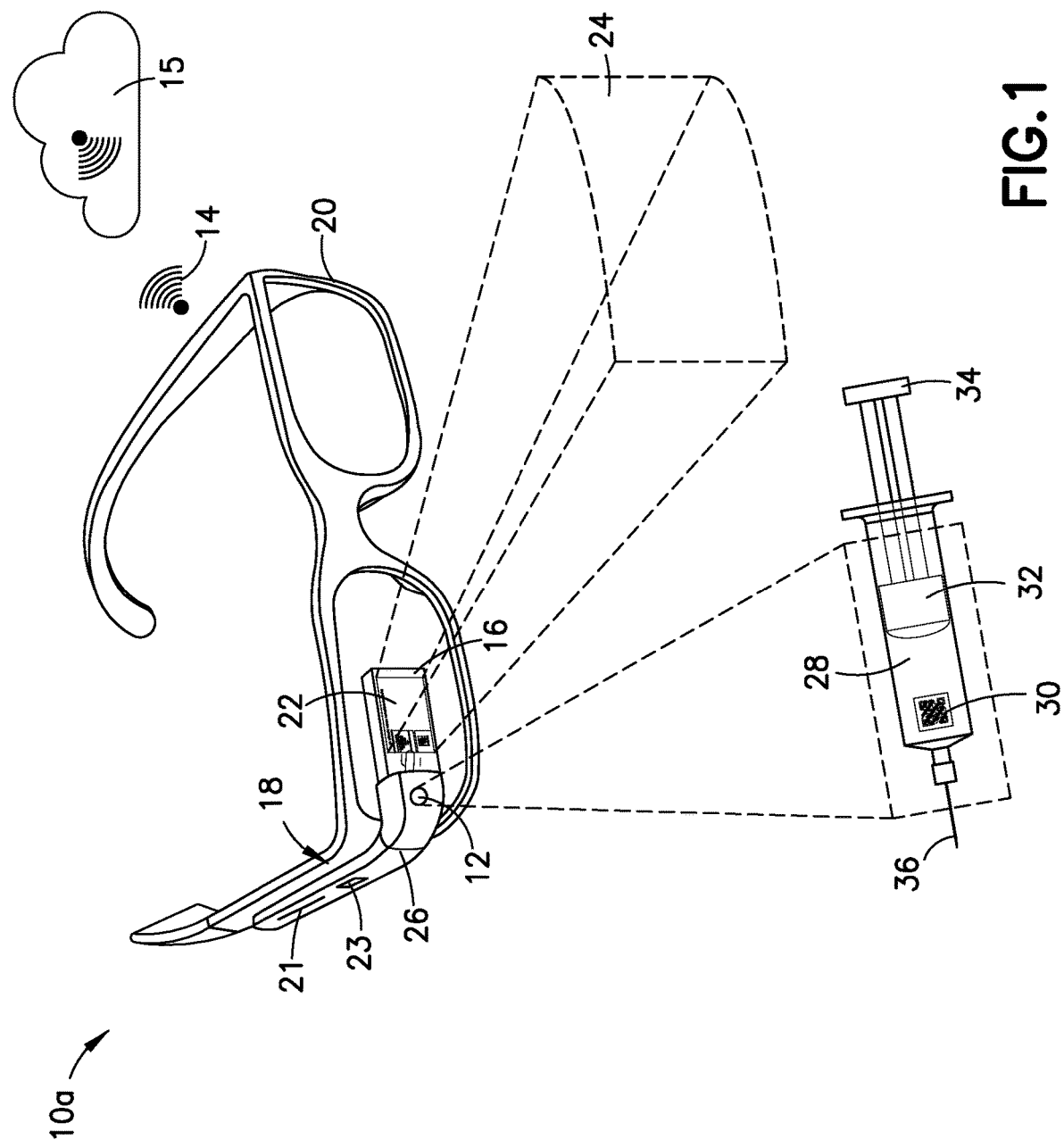
FIG. 1 is a schematic representation of a hands-free system for assuring patient medication and fluid delivery according to the principles of the invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. For the purpose of facilitating understanding of the invention, the accompanying drawings and description illustrate preferred embodiments thereof, from which the invention, various embodiments of its structures, construction and method of operation, and many advantages may be understood and appreciated.

The present invention is directed to systems and methods for hands-free identification, confirmation, and documentation of various medical procedures at the clinical point of use, including invasive procedures requiring procedural guidance. Example procedures include, but are not limited to, medication and fluid delivery, specimen or sample collection, and/or vascular access procedures. The system improves on existing patient data systems by collecting and recording data without requiring affirmative acts by a user or operator, referred to hereinafter as a medical technician. More specifically, the systems allow a user or operator, referred to hereinafter as a medical technician, to perform necessary identification, conformation, and documentation activities without being required to manually record information or manipulate data input devices, such as scanners, cameras, keyboards, or touchscreens, as is required by presently existing patient data systems. The system improves clinical workflow and data input integrity by reducing the possibility of technician error. Additionally, the system reduces the risk of infection for patients and medical technicians. Specifically, since the medical technician is not required to touch or operate a data input device, the risk that the input device would become contaminated is reduced.

The system may be integrated with existing equipment, including disposable medical devices already being used, as well as existing patient databases and patient monitoring software. Thus, the system does not require additional equipment or capital infrastructure improvements on the part of the medical facility. Similarly, the system can be easily integrated with procedures and practices of a specific medical facility.

With reference to FIG. 1, a system 10a for hands-free assurance and verification of fluid delivery to a patient at the clinical point of use is illustrated. The system 10a effectively obtains data about the fluid delivery to be performed from an external source, such as a patient data system, documents that the fluid procedure is performed, and sends confirmation of the procedure to an external source. The system 10a is provided for the purpose of reducing the risk of medication error at the point of administration by providing real-time patient information, alerts, medication identification, and dose confirmation in a hands-free manner.

The system 10a includes a wearable electronic device. In a preferred and non-limiting embodiment, the wearable electronic device is a wearable computer with an augmented reality display, referred to hereinafter as a "wearable electronic device 18". An exemplary wearable electronic device 18 may be a head-worn device, such as glasses incorporating Google Glass technology, created by Google Corp., of Mountain View, Calif. While the Google Glass technology is not presently commercially available, it is believed that once Google Glass or a similar product becomes commercially available, it could be easily implemented into the invented system by one having ordinary skill in the art. Alternatively, the wearable electronic device 18 may be a head-worn face-shield also incorporating Google Glass technology. In a further embodiment, the wearable electronic device 18 may be a wrist-mounted device also incorporating Google Glass technology. The wearable electronic device may also have other shapes and configurations, based on the particular fluid delivery procedure being performed. For example, the wearable electronic device may be a button or pin attached to the medical technician's clothing, a watch worn about the wrist, necklace, pendant, or any other sort of unobtrusive and easily carried item.

The wearable electronic device 18 may include a hat, helmet, face shield, wristband, or frame 20 (e.g., a frame for a pair of glasses) having a display portion 16, such as a projection prism, face shield, or wrist worn display that extends into the field of view of the medical technician. The display portion 16 may be placed in close proximity to a wearer's eye, such as in the case of a projection prism. The display portion 16 is configured to present a virtual layer, such as the projected layer of FIG. 2, within the wearer's field of view that is equivalent to a larger screen viewed from a farther distance away. For example, in the instance of the display portion 16 being a projection prism, the projection prism may be positioned less than an inch from the wearer's eye, but presents a viewable screen that appears as a 25 inch screen viewed from 8 feet away. The augmented reality display projects a virtual projection or layer 22 that covers a portion of the wearer's field of view. The medical technician's entire field of view is not obscured by the virtual layer 22. The medical technician can still "see" a reality layer 24 beyond or adjacent to the virtual layer 22.

In other embodiments, the data display portion 16 of the wearable electronic device 18 may be a visual display, such as a standard monitor for a computer or smart phone. Standard monitors include liquid crystal displays (LCD) and light emitting diode (LED) displays. The monitor may be integrally formed with the wearable electronic device or may be an external screen or device viewable by the technician. The wearable electronic device 18 may also communicate treatment and patient information to the technician through other communication means including, but not limited to, audio alerts or tactile confirmation. For example, the wearable electronic device 18 may beep or vibrate to signal to the technician that a problem was identified.

The wearable electronic device 18 further includes a computer housing 26 or enclosure attached to the frame 20. The housing 26 may be any size necessary to hold the required associated electronics. The associated electronics within the computer housing 26 may include data collection devices and sensors, data transmission and communication circuitry, data processing circuitry, and data display and alert devices and circuitry. Desirably, the computer housing 26 is small and lightweight enough that it does not pose a substantial hindrance to a wearer or operator as the operator performs normal functions and activity.

The data collection devices may include a variety of sensors and recorders for obtaining information about the medical procedure being performed. For example, the data collection function may include one or more image capture devices 12, such as digital cameras, for image or video capture. In certain embodiments, the image capture device 12 may be adapted to provide a still or running two-dimensional image or images, or a three-dimensional anatomical scan geometry. An image or video camera usually consists of a charge-coupled device (CCD) or complementary metal-oxide-semiconductor (CMOS) imaging sensor, a lens, a multifunctional video control/digital signal processing (DSP) chip, and a set of discrete components (e.g., capacitor, resistors, and connectors). The video control/DSP chip may be integrally formed with the camera 12. Alternatively, image processing may be performed elsewhere on the wearable electronic device, or even at an external controller or computer. The lens may include a focus range useful for imaging as described herein or the video cameras may include an auto-focus feature. Likewise, the lens may be equipped with a zoom functionality. While the video control component on the chip performs a number of image acquisition tasks, the DSP component on the same chip implements data processing algorithms, such as noise reduction and simple forms of data compression and encryption. The digital output from the video control/DSP chip may be in either a parallel or a serial form, depending on the particular chip design and the input configuration in the next data processing or interface stage. The system may also include microphones for auditory (e.g., voice command) input, touch mechanisms or track pads for tactile input, accelerometers, gyroscopes, and the like.

The electronic communication and data transmission devices and electronic circuitry may include a data transmission interface 14 for sending and receiving data to and from external sources, such as an external electronic device. The external device may be a data storage device, external computer, a local computer network consisting of a number of computing devices, or the Internet. For convenience, these external electronic devices will be collectively referred to as the cloud 15. The data transmission interface, in effect, creates a personal area network (PAN) including the wearable electronic device 18, a data transmitter and an external receiver attached to an external source. A PAN is a computer network used for communication (e.g., data transmission) among computer devices including telephones and personal digital assistants (PDAs) in close proximity to the technician's body. PANs can be used for communication among the personal devices themselves (intrapersonal communication), or for connecting to a higher level network and the Internet (an uplink). Networks may be wired using, e.g., USB, ethernet, and FireWire protocols. A wireless personal area network (WPAN) is made possible with wireless network technologies such as Bluetooth®, WiFi, Z-Wave, and ZigBee. WiFi (e.g., IEEE 802.11a, b, g, n) networking protocols may be used, which advantageously have a greater transmission range than Bluetooth®, but consequently also have greater power consumption. Suitable external sources for receiving data transmitted from the device and optionally processing the data include a computer, tablet PC, or smart phone and/or an external hard drive or other device for backing up stored data.

In certain embodiments, the data transmission interface 14 is integrated with an existing patient data system or database. Mobile patient data acquisition and recording systems integrated for use with handheld electronic devices, such as smart phones, may also be integrated with the data transmission interface 14. These systems may allow users to remotely update patient data using the handheld electronic device. The updated information is transferred to a data storage location, where it can be accessed for future use. Commercially available software platforms may be used to coordinate recording patient data, and may include features for making such data easily accessible at the point of care. As a result of integration with such existing database software platforms, the presently invented system 10a is capable of automatically updating patient data stored on a patient data system or database as a procedure is being performed. However, unlike existing systems, the present system 10a updates patient data automatically, without direct input from the medical technician. Thus, the system 10a is fully and automatically integrated to the patient data system. In contrast, previously, data was manually entered by the medical technician after a procedure was performed.

In certain embodiments, the wearable electronic device 18 may also include a data storage device 21 integrally formed with the computer housing 26. In one non-limiting embodiment, the storage device 21 is a digital data recorder, such as a disk drive, which records data onto a storage medium. In another embodiment, the storage medium is flash memory. The storage medium is any type of non-volatile memory, for example, magnetic data storage media such as a hard disk drive or magnetic tape, or flash-based memory. Flash memory is a non-volatile computer storage chip using NAND or NOR type memory as found in MicroSD cards, USB flash drives, or solid-state drives. File systems optimized for flash memory (solid state media) include Embedded Transactional File System (ETFS), exFat, and FFS2 systems. The storage medium can be random access memory (RAM) or read only memory (ROM). The memory may be removable from the device or permanently installed within the housing and transferable to an external device through the data transmission interface 14.

In one embodiment, the wearable electronic device 18 further includes one or more power supplies, such as a battery 23 included in the computer housing 26. A battery 23 comprises one or more electrochemical cells that convert stored chemical energy into electrical energy. One non-limiting example of a useful battery is a lithium-ion battery. A lithium-ion battery is a rechargeable battery often used in electronic devices. It is preferable that the capacity of the lithium-ion battery is sufficient to power the wearable electronic device for an entire day, or longer. In some cases where the device is not operated continuously, however, a battery of smaller capacity is more appropriate for reduced device size and weight. Other types of batteries adaptable for use in the device include nickel cadmium (NiCd) and nickel metal hydride (NiMH) batteries. Preferably the battery 23 is rechargeable and, in that case, the device further includes a battery recharge port.

The electronic devices and electronic circuitry included in the housing 26 of the wearable electronic device 18 are controlled by one or more controllers, such as microprocessors. A microprocessor is a chip containing one or more integrated circuits which receives data and processes the data according to instructions stored in the chip's memory. A microprocessor typically, along with other functions, manages the collection of data from the various sensors and the digital cameras 12, directs the storing of data by the data storage system, and allocates system resources between the electronic components to reduce power consumption and decrease the need for duplicative electronic systems. The microprocessor may include software for controlling various data collection and software for processing collected data. Similarly, the microprocessor may include software for displaying collected data, as well as for interacting with the technician. Alternatively, the controller may facilitate transfer of data and instructions between the wearable electronic device and an external processing device, such as an external computer or workstation.

With continued reference to FIG. 1, the system 10a includes a fluid delivery apparatus 28, such as a pre-filled syringe, pen injector, auto-injector, infusion set, catheter, or any combination thereof. The wearable electronic device 18 is configured to identify and recognize the fluid delivery apparatus 28. To facilitate identification and recognition, the fluid delivery apparatus 28 may include an identification tag 30 integrally formed with or affixed thereto. The identification tag 30 may be a standard two-dimensional bar code, three-dimensional bar code (e.g., a quick read (QR) code), as well as various proprietary encoded computer-readable tags and labels, as are known in the art. The identification tag 30 may be integrally formed on or within the fluid delivery apparatus 28. Alternatively, the identification tag 30 may be printed on the fluid delivery apparatus 28 or printed on a label that is adhered to the fluid delivery apparatus 28. In either case, the wearable electronic device 18 is configured to identify the identification tag 30 and to extract information therefrom. The identification tag 30 may provide information about the fluid delivery apparatus 28 and fluid contained therein, including medication type, total fluid volume, manufacturer, needle dimensions, fluid expiration date, and the like.

In certain embodiments, the wearable electronic device 18 may include image processing functions for identifying and extracting data from an image of the identification tag 30 captured by the digital camera 12. The image processing function may be configured to identify various positional markers on the fluid delivery apparatus 28. The positional marker may point to the identification tag 30 and may trigger the wearable electronic device 18 to begin capturing images of the identification tag 30. Once a suitable image is captured, the image processing function evaluates the image and extracts information from the identification tag 30. The image processing function may also include a time delay of, for example, three (3) seconds, meaning that the wearable electronic device 18 does not begin attempting to process or read the image of the identification tag 30 until the positional marker has been in the field of view for at least three seconds. The time delay function preserves computing capacity by restricting when image processing occurs. Particularly, only identification tags 30 that are interesting enough for the technician to view for several seconds are scanned to extract information therefrom. In certain embodiments, identification tags 30 that are not within the technician's field of view for at least three seconds are assumed to be unimportant and, as such, are not read.

Alternatively, the identification tag 30 may be a standard medical label including the name of the medication or therapeutic agent and volume in standard printed characters. The wearable electronic device 18 may be configured to capture an image of the label and to read the information contained thereon. For example, the system 10a may include an optical character recognition algorithm configured to extract data from printed text, such as a printed medical label. Thus, the system may be used with existing fluid delivery apparatuses 28 and syringes and may not require that additional tags or electronic locator devices be added.

In another alternative embodiment, the identification tag 30 may be a near field communication (NFC) device, such as a radio frequency identification (RFID) tag or electronic device capable of projecting a readable signal that could be identified and read by a scanner, transmitter, or antenna associated with the wearable electronic device 18. Inclusion of an NFC device, or RFID tag, simplifies the data extraction process. Particularly, no image processing is required to extract information from the NFC device or RFID tag.

In certain embodiments, the identification tag 30 may be printed or attached to the fluid delivery apparatus 28 using a selectively visible type of ink that is only readable at particular times, such as just before fluid delivery occurs. After fluid delivery is complete, a different or modified identification tag 30 may become visible to signify end of use or that an injection is completed.

The system 10a may also include means for identifying when fluid delivery has occurred and, optionally, for estimating the fluid delivery volume. The system 10a may monitor fluid delivery by tracking movement of an actuation mechanism or fluid expulsion mechanism, such as a plunger 32 or piston rod 34, during the fluid delivery procedure. In certain further embodiments, the identification tag 30 may be used to estimate the position of the plunger 32 or piston rod 34. For example, image processing software could record the initial position of a plunger 32 or piston rod 34 relative to the position of the identification tag 30. When the plunger 32 or piston rod 34 moves relative to the position of the identification tag 30, the image processing software determines that an injection has begun. When the plunger 32 or piston rod 34 advances a predetermined distance from the identification tag 30, it may be assumed that the injection is complete.

The system 10a may also be configured to automatically identify the position of the plunger 32 or piston rod 34 relative to other markers on the fluid delivery apparatus 28. In certain embodiments, the markings could be graduated lines or indicia on a syringe barrel. In that case, the movement of the plunger 32 or piston rod 34 relative to the markings could determine not only initiation and dose, but also fluid volume delivered. In further embodiments, the plunger 32 may include a coating or indicator that is easily identifiable on an image captured by the digital camera 12. Alternatively, the coating could be easily detectable from another scanning element, such as an ultraviolet light or infrared detector. Such a device or scanner could be associated with the wearable electronic device 18. Enhancing the visibility of the plunger 32 improves recognition by the image processing functionality and may improve volume estimation by allowing for more exact determination of plunger 32 location.

In certain embodiments, additional electronic or mechanical sensors could be associated with the fluid delivery apparatus 28 to provide further evidence or confirmation of fluid delivery. For example, sensors could be placed near an injection needle 36 of the fluid delivery apparatus 28. The sensors may record when the needle 36 is correctly inserted in a patient and ensure that fluid passes through the needle 36 and is expelled to the patient. Data collected by the sensors could be transmitted to the wearable electronic device 18 by a wireless transmitter, desirably a wireless transmitter, such as Bluetooth®, adapted for short range communication. Including a sensor directly on the fluid delivery apparatus 28 increases the complexity of the fluid delivery apparatus 28 and associated electronics, but, advantageously, provides additional assurance that fluid delivery to a patient actually occurs.

In addition to being used to locate and read the identification tag 30 and to provide end of dose confirmation, the image capture functionality of the wearable electronic device 18 may also be relied upon to archive and document the fluid delivery procedure. For example, images of the injection process (e.g., the insertion of the needle into the patient's vein), an image of an empty syringe, and an image of a discarded syringe could be obtained and included in the patient's electronic record. Each of these images may be embedded with a time stamp. The time stamp could be used to update the patient's medical record with the exact time when a procedure was performed.

The wearable electronic device 18 is configured to present data collected by the image capture and other functions of the system to the technician in an easy to use and easily accessible manner. Desirably, data is presented to the technician in a clear and concise manner directly within the technician's field of view via the display portion 16 of the wearable electronic device 18.

Figure 2:
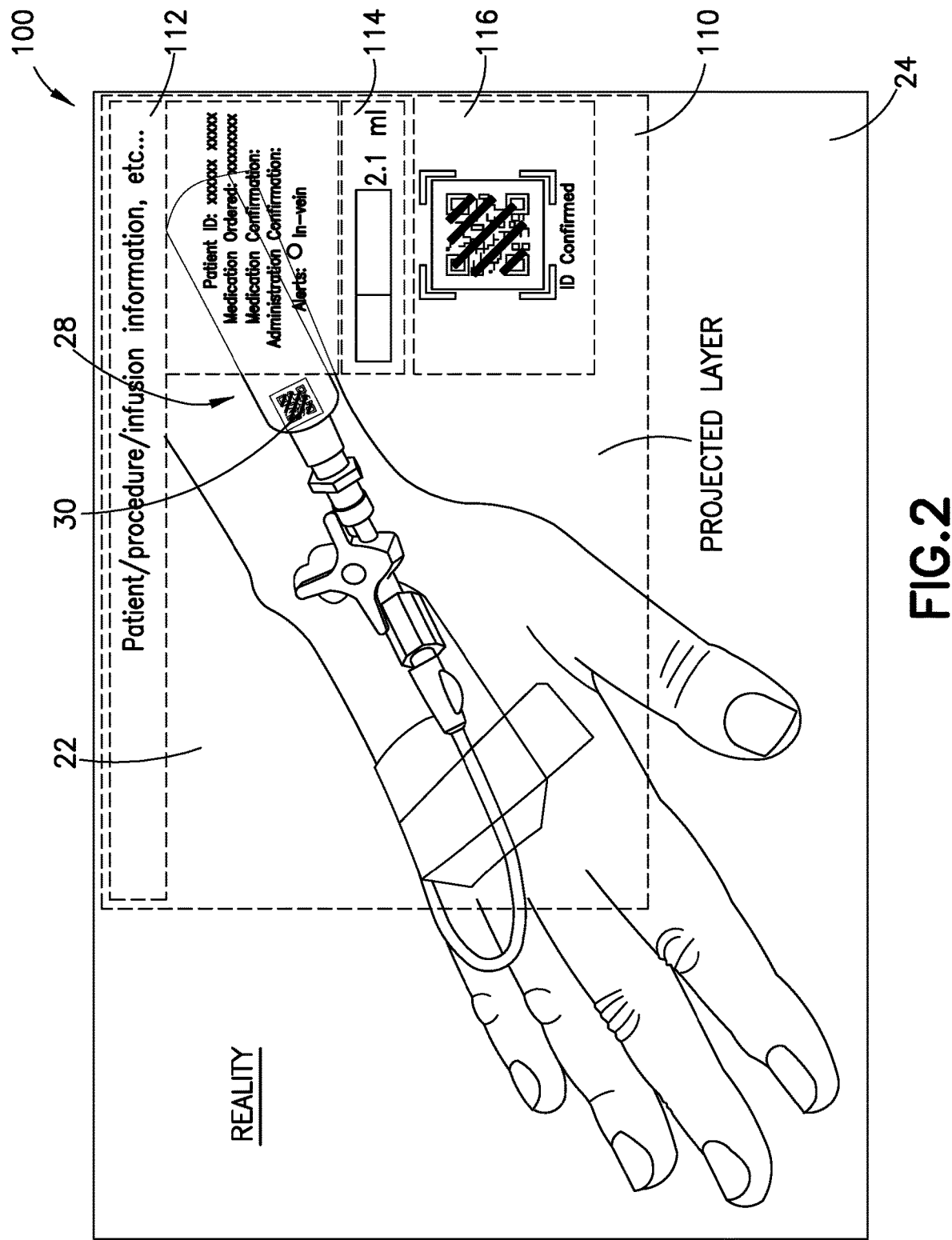
FIG. 2 is a schematic representation of a field of view display for the system of FIG. 1.

An exemplary field of view 100, as seen by a technician wearing a wearable electronic device 18 and including both the virtual layer 22 and reality layer 24, is depicted in FIG. 2. As shown in FIG. 2, the virtual layer 22 includes a user interface 110. The user interface 110 may include a heading bar 112 or title with information about the patient, such as the patient's name and patient identification number. The heading bar 112 or title may also include a description of the medical procedure to be performed or information about the type of injection or fluid delivery device required. The user interface 110 may also include a syringe volume indicator icon 114 showing estimated fluid remaining in the syringe. The icon 114 allows the operator to easily determine when all fluid is injected to the patient and, thus, acts as an end of dose indicator. Finally, the user interface 110 may also display an identification tag confirmation icon 116. The icon 116 could show when an identification tag 30 has been identified on an image obtained by the image capture functionality. Furthermore, the identification tag confirmation icon 116 could show confirmation that the identification tag 30 is correct, such as when the fluid delivery apparatus 28 needed for the particular procedure being performed is recognized. If the identification tag 30 cannot be located or if an incorrect identification tag 30 is found, the icon 116 may display an alert, signifying to the technician that the injection should not be performed.

As described above, the virtual layer 22 does not block the operator's entire field of view 100. Thus, the operator still sees the reality layer 24 even when the user interface 110 is in view. Accordingly, the technician can see any alerts while preparing to perform the procedure. As a result, the possibility that the technician would miss an alert because he or she is busy preparing for the fluid injection is effectively reduced.

With reference to FIG. 3A, a system 10b for assuring patient medication or fluid delivery, according to a further embodiment, is illustrated. The system 10b includes a wearable electronic device 18 having a frame 20 in the form of head-worn glasses. In the system 10b of FIG. 3A, the wearable electronic device 18 may be used to visualize the fluid delivery apparatus in step (a), as described elsewhere herein, and to visualize a patient ID 38 in the form of a wristband 40 worn about the patient's wrist, in step (b). It is noted herein that steps (a) and (b) may be accomplished in any order. The wristband 40 includes an identification tag 42 with a QR code. The patient ID 38 may also include a unique visual marker or indicia near the identification tag 42 or QR code to trigger the image capture functionality of the wearable electronic device 18. When the unique marker is identified, the wearable electronic device 18 having a frame 20 in the form of head-worn glasses begins processing the captured image to find and read the QR code. The patient ID 38 may also include additional encoding or identification technologies, such as an NFC tag (e.g., RFID), visual coding, such as text, that can be identified and read by image processing functionality, Bluetooth® or similar short range data transmission antenna, and other proximity sensing technologies. The patient ID 38 includes information about the patient and may, optionally, be linked directly to an electronic patient record on a patient data system. The patient ID 38 may further include location-providing technology, such as GPS, for determining the location of the patient. The technician can scan the patient ID 38 to obtain information about the patient, such as the procedure to be performed, or a schedule for when future fluid deliveries should be performed, as well as any known medical conditions of the patient. Since the patient ID 38 links the wearable electronic device 18 to the patient's electronic record, any information or documentation taken during the procedure, such as time of the injection, duration of injection, or amount of fluid injected, can be transmitted to and stored with the patient's electronic record. As discussed herein, the display of information is provided to the wearer of the wearable electronic device 18 in the glasses-mounted display 16, as described with reference to FIG. 1.

Figure 3B:
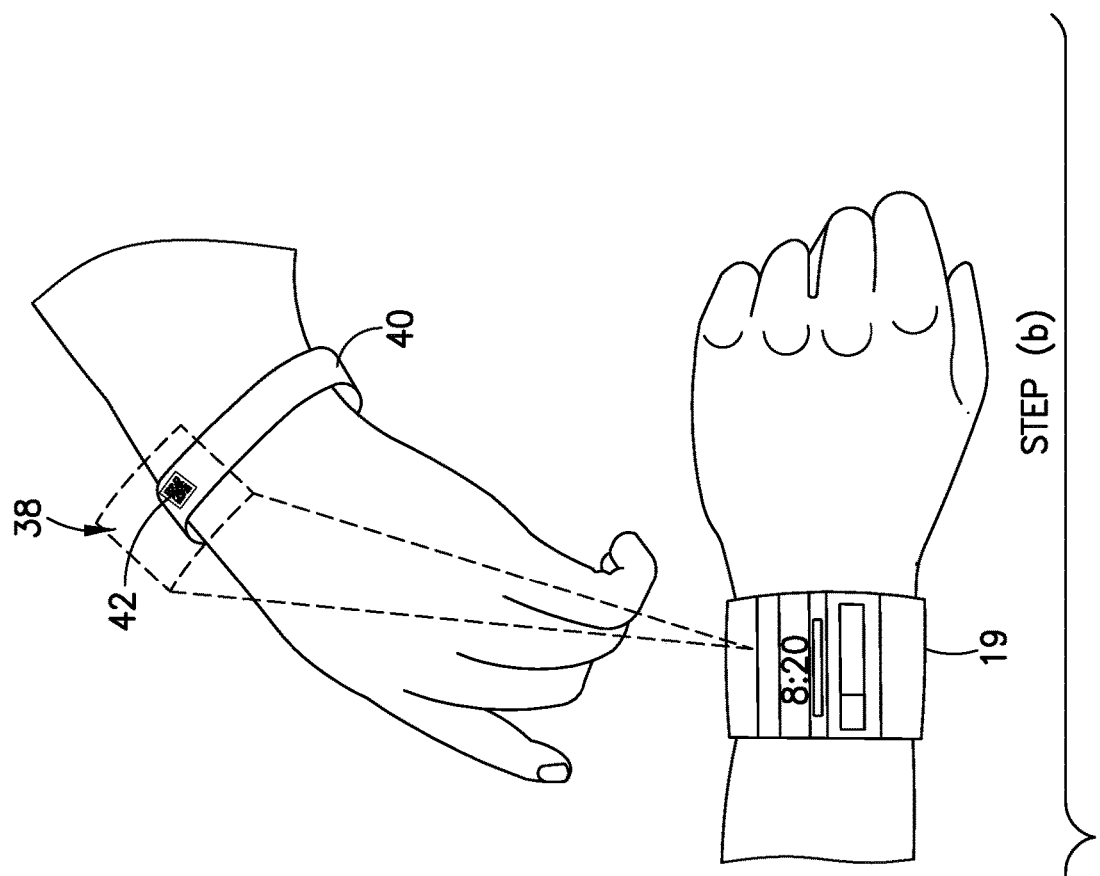
FIG. 3B is a schematic representation of a hands-free system for assuring patient medication and fluid delivery having a wearable device in the form of a wrist-mounted device and a patient identification device, according to the principles of the invention.
Figure 3B:
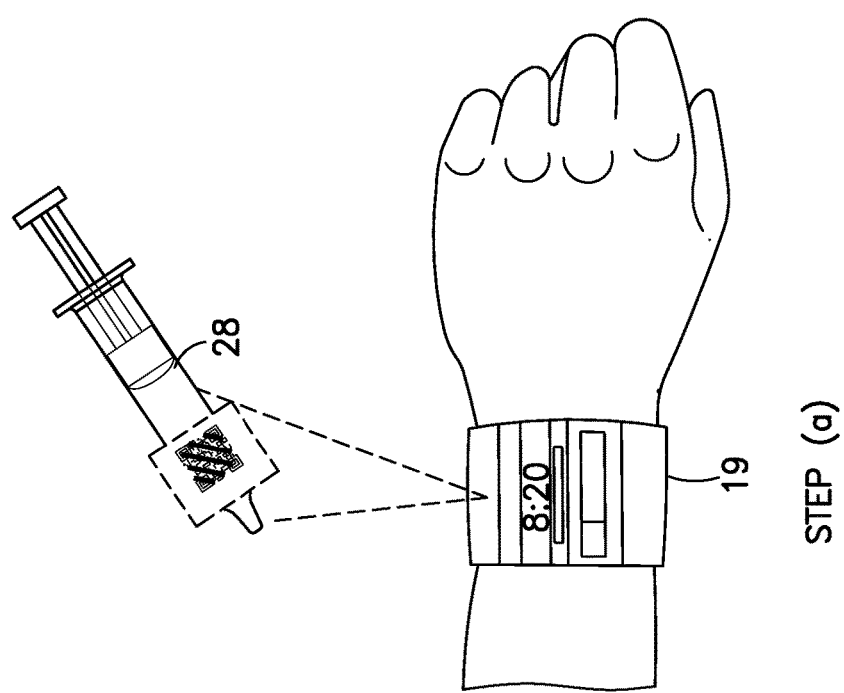

With reference to FIG. 3B, a system 10b for assuring patient medication or fluid delivery as described above with reference to FIG. 3A is shown in which the wearable electronic device 18 is provided in the form of a wrist-mounted display 19, such as a SmartWatch. The system of FIG. 3B functions similarly to the system of FIG. 3A, with the exception that the display 16 is coordinated through the wrist-mounted display 19, which provides similar functionality to the display 16, as described herein but with a physical positioning on the wrist of the user. In the system 10b of FIG. 3, the wearable electronic device 18 may be used to visualize the fluid delivery apparatus in step (a), as described elsewhere herein, and to visualize the patient ID 38 in the form of a wristband 40 worn about the patient's wrist, in step (b). It is noted herein that steps (a) and (b) may be accomplished in any order.

Figure 4:
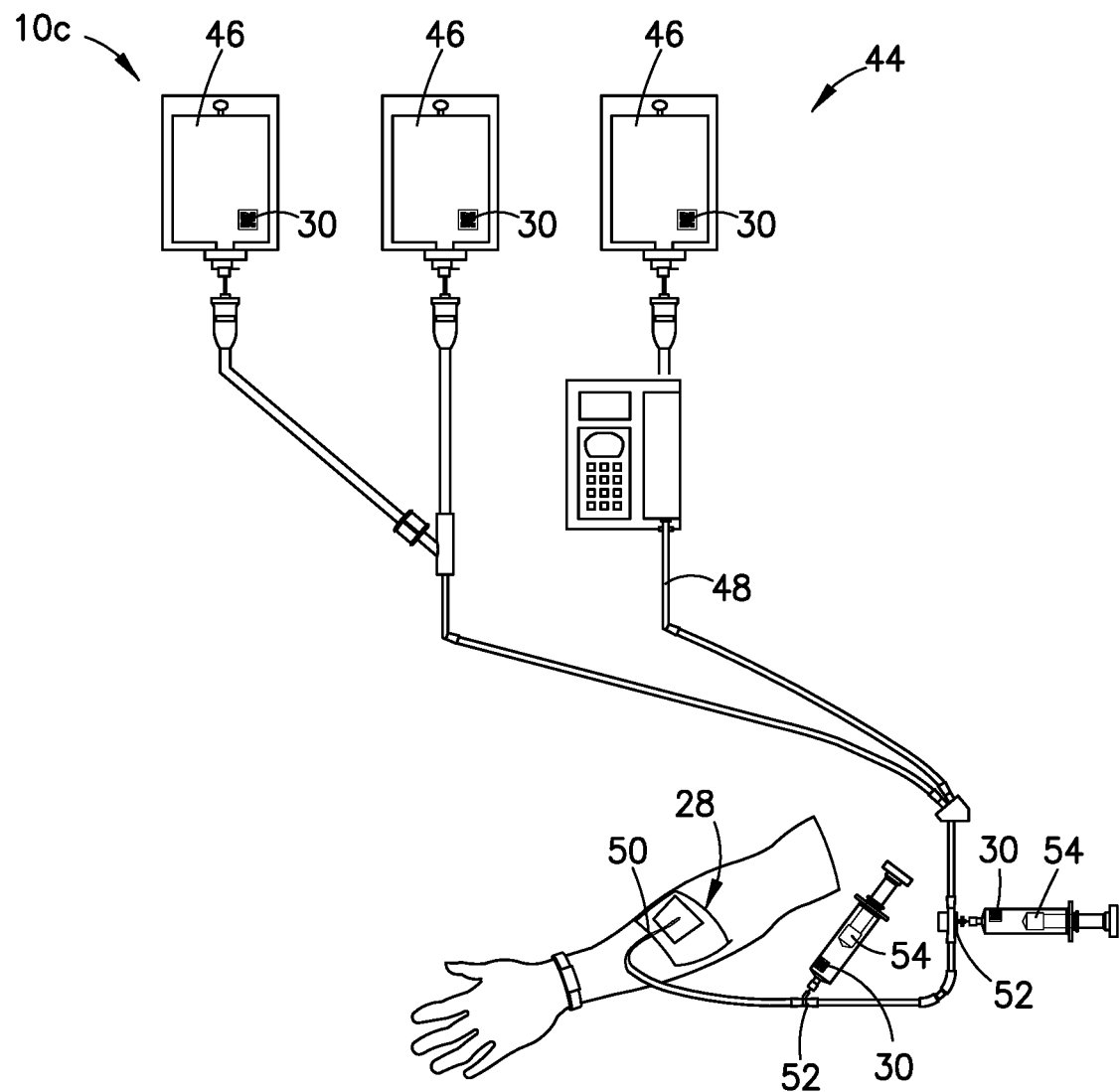
FIG. 4 is a schematic representation of a hands-free system for assuring patient medication and fluid delivery, according to the principles of the invention.

With reference to FIG. 4, a further embodiment of a system 10c for assuring fluid delivery to a patient is depicted. The system 10c is used for administering fluid to a patient through a fluid delivery apparatus 28, such as an infusion set 44, including various fluid containers 46, namely intravenous therapy (IV) bags, associated tubing 48, and a catheter 50 extending into the vein of a patient. The tubing 48 may further include one or more access ports 52. Syringes 54 can be connected to the access ports 52 for providing additional or different types of medical fluid to a patient. As in previously described embodiments, the system 10c includes a wearable electronic device 18, the fluid delivery apparatus 28, and identification tags 30 readable by the wearable electronic device 18. The identification tags 30 include or are associated with identifying information about the fluid delivery apparatuses 28. The system 10c confirms the procedure to be performed and fluid to be injected, identifies the devices and apparatus needed, confirms that fluid is being administered to the patient, and documents the procedure.

In certain embodiments, the system 10c may be configured to confirm that the infusion set 44 is correctly installed and connected. For example, the image processing functionality may identify various connection points of the infusion set 44, fluid containers 46, and catheter 50. The system 10c would then confirm that the elements are connected correctly. If a suitable connection is not recognized, the system 10c may alert the technician to check the connection before beginning the fluid delivery. The system 10c may also provide various other device maintenance alerts. For example, the system 10c may alert the technician when a predetermined indwell time limit is reached. Similarly, the system 10c may alert the technician at various intervals when system maintenance should be performed.

In certain further embodiments, the system 10c is configured to visually monitor drip count of the infusion set 44 to establish and confirm fluid delivery rates. For example, the image capture functionality of the wearable electronic device 18 may document the time of insertion of the catheter 50. The image capture functionality will then record the outflow port of the fluid container 46 for a predetermined period of time to record drops of fluid flowing from the container 46 into the infusion set 44. The image processing functionality of the wearable electronic device 18 identifies individual fluid drops to estimate fluid delivered to the patient over a period of time. The system 10c may be configured to provide an alert when a sufficient period of time has passed for delivery of a predetermined fluid volume.

With reference to FIGS. 1-4, when using the system 10a, 10b, 10c the technician puts on the wearable electronic device 18. For example, the technician may put on the wearable electronic device 18 at the beginning of a shift, or before starting to perform a particular injection or fluid delivery procedure. When the wearable electronic device 18 is in place and turned on, the wearable electronic device 18 may display a start screen providing the technician with initial instructions, such as a task list with patients to visit and procedures to perform. The wearable electronic device 18 may also ask the technician to confirm his or her identity to ensure that the correct individual is given the correct instructions. When first coming into contact with a patient, the technician uses the wearable electronic device 18 to capture an image of the patient ID 38. Based on information on or associated with the patient ID 38, medical information about the patient, including the injection to be performed, is obtained. The obtained information is displayed on the user interface 110, along with instructions for performing the procedure. Based on the displayed instructions, the technician may obtain items needed for the injection, including an appropriate fluid delivery apparatus 28 and, if necessary, a medical fluid vial or cartridges to load into the fluid delivery apparatus 28. When the operator "sees" the injection apparatus and other items in his or her field of view 100, the wearable electronic device 18 identifies and reads identification tags 30 attached to the items. The system 10a, 10b, 10c may check the obtained medical items to ensure that only items necessary for the procedure are obtained and to ensure that no additional items are needed. As items are obtained and identified by the system, the instructions on the user interface 110 are updated. For example, if a correct item is obtained, a confirmation message may be displayed to the user interface 110. If an incorrect item is obtained, an alert may be presented to the technician. The alert may be visual, such as an icon displayed in the user interface 110, as well as tactile, auditory, or any combination thereof.

Once the items are obtained, the technician performs the medical procedure. As the technician performs the procedure, the injection activities are monitored to verify the injection. For example, the wearable electronic device 18 may ensure that the needle 36 is inserted into the skin of the patient and may ensure that fluid is expelled from the fluid delivery apparatus 28. Information, including the time and date of the injection and name of the technician, may be recorded and transmitted to an external system, such as a patient data system. Thus, the collected information may be automatically included in the patient's digital record. The information may also be transmitted for billing purposes or, if necessary, to third party insurers.

In certain further embodiments, the time and date information can be used for establishing a baseline for future medical procedures. The baseline may be used to determine for how long an infusion should be performed, or to set times for checking the infusion set 44. Similarly, in the case of injections from syringes or injectors, the baseline time data can be used to schedule subsequent treatments. Based on this information, the system 10a, 10b, 10c may be configured to show warnings or alerts in the user interface 110 when the subsequent treatment should be provided.

Figure 5:
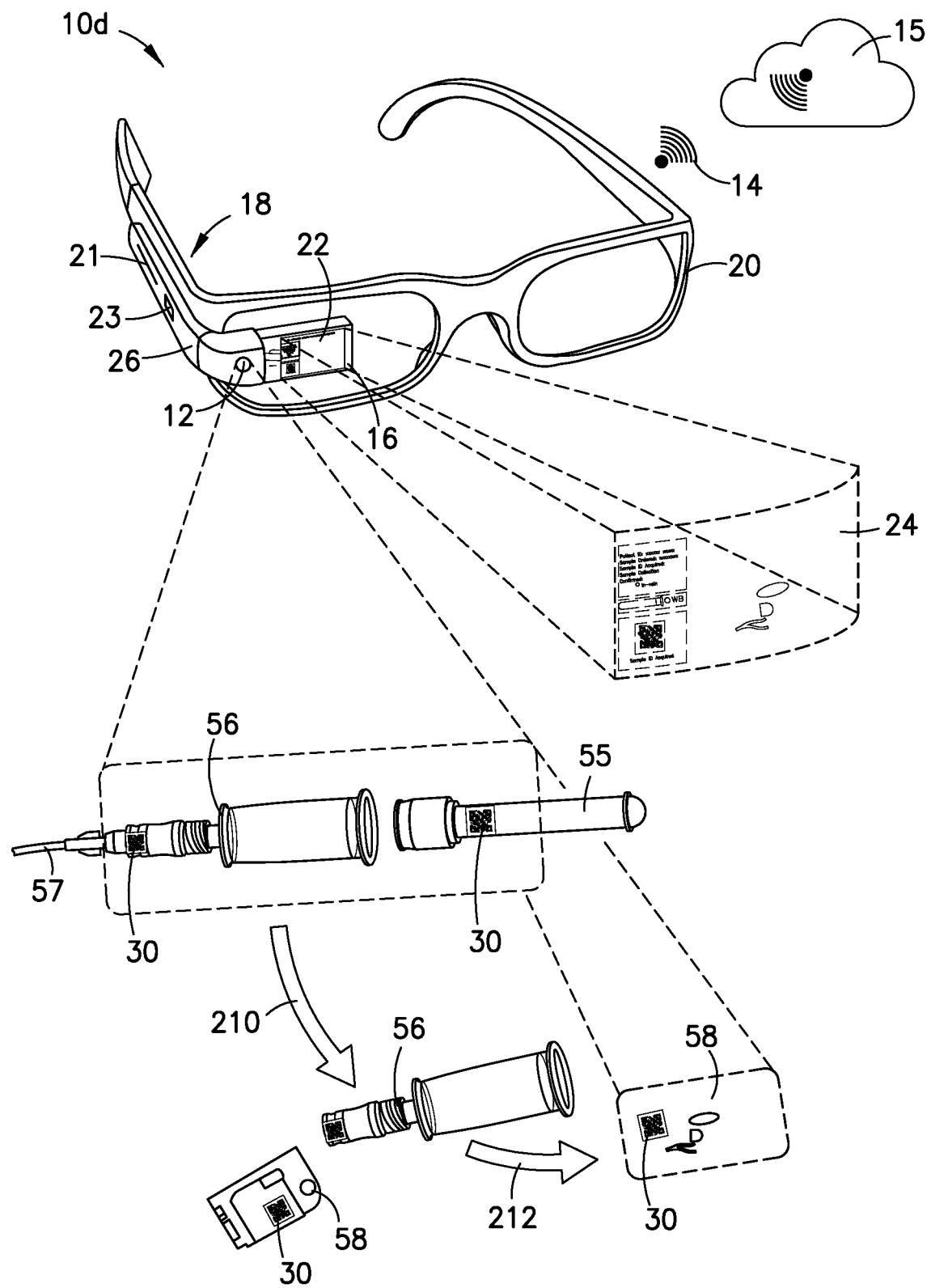
FIG. 5 is a schematic representation of a hands-free system for establishing identification of a test specimen and for sample tracking, according to the principles of the invention.
Figure 6:
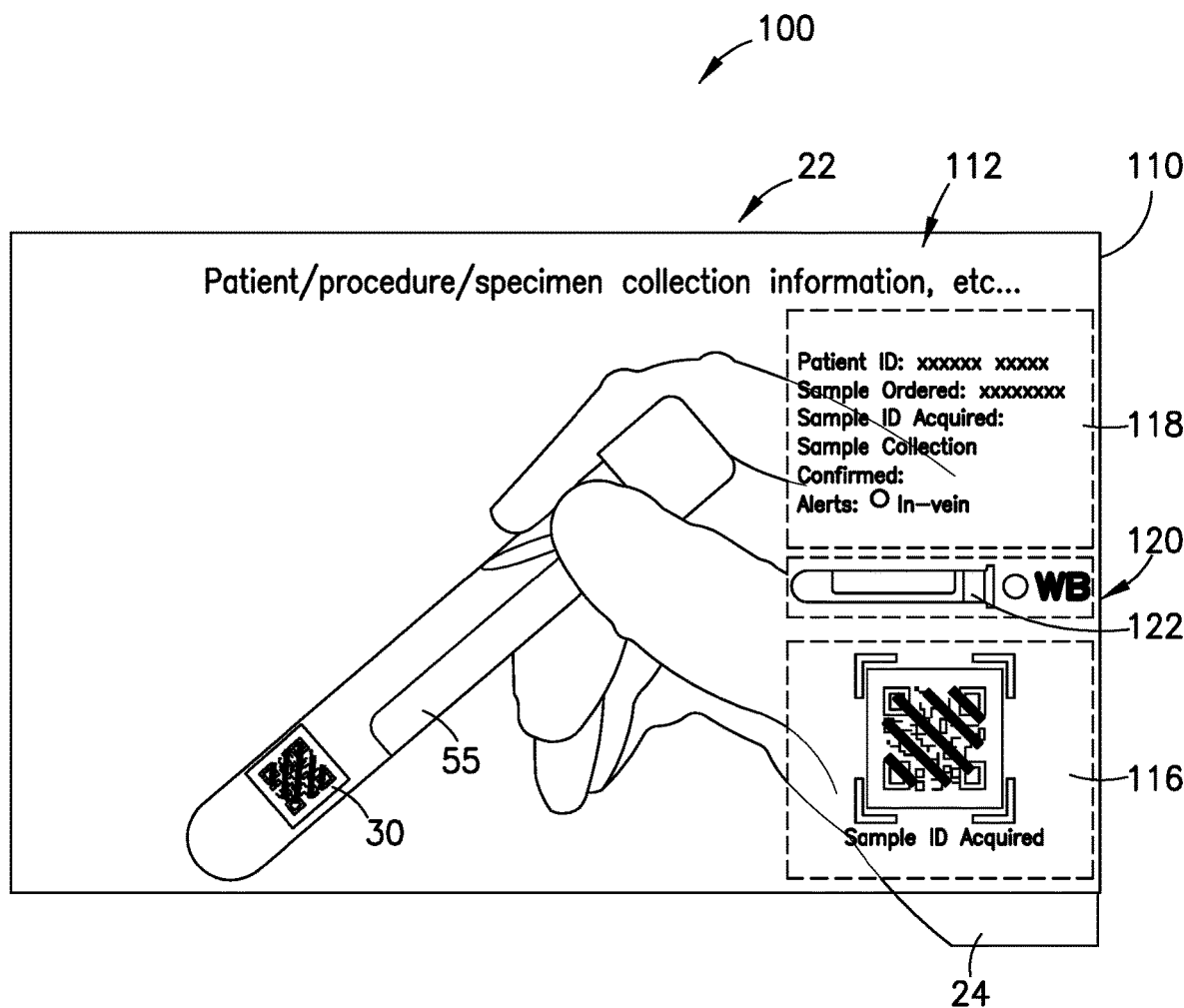
FIG. 6 is a schematic representation of a field of view display for the system of FIG. 5.
Figure 7:
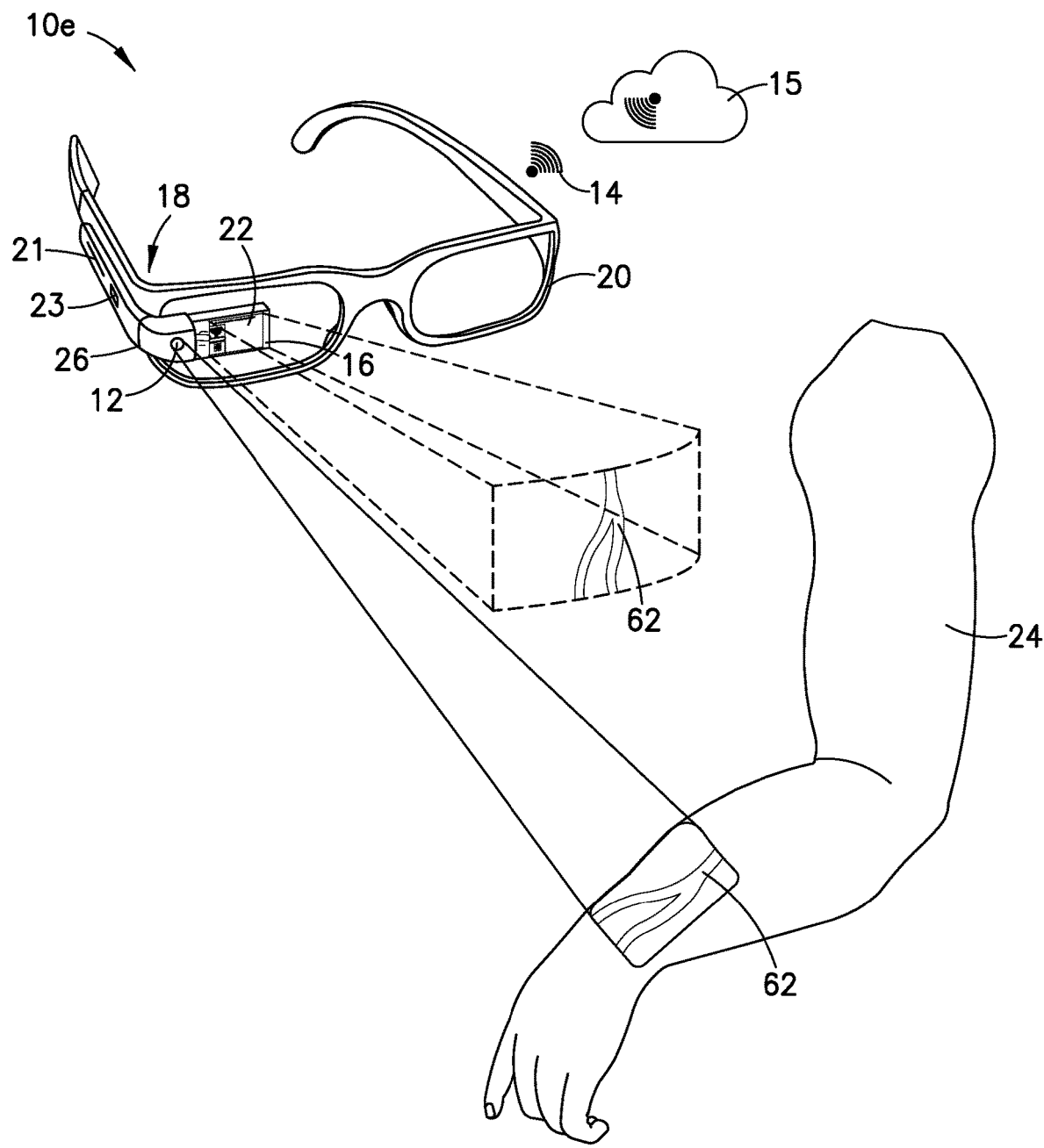
FIG. 7 is a schematic representation of a system for enhanced visualization during insertion of an invasive device, according to the principles of the invention.

According to another aspect of the invention and with reference to FIGS. 5 and 6, a system 10d and method for obtaining a test specimen for medical testing and diagnosis is illustrated. Advantageously, the system 10d provides for an automatic, non-clinically disruptive, hands-free way to establish specimen identification, collection confirmation, sample and results tracking, and integration into the patient data information system. The system 10d is configured to track the chain of custody of a fluid sample starting at the time the sample is obtained and may continue through sample testing or reporting results. Furthermore, the system 10d may be automatically integrated with existing patient data systems, so that information about the type of sample to be collected and tests being performed can be displayed to the technician.

As in previously described embodiments, the system 10d includes a wearable electronic device 18. The system 10d also includes a blood sampling device 56, which may be part of a larger extravascular fluid collection system. The blood sampling device 56 provides a fluid connection between the larger extravascular fluid collection system and the interior of a specimen collection container 55. The blood sampling device 56 generally includes a spike or port at a distal end thereof. The specimen collection container 55 can be inserted onto the spike or port for collection of a fluid sample through the blood sampling device. The blood sampling device 56 may also be configured to release a small amount of fluid sample, such as a discrete number of fluid drops, through a proximal opening of the blood sampling device 56. The extravascular system includes the blood sampling device 56, the specimen collection container 55, extension tubing 57, and an invasive access device, such as a vascular access device (shown in FIG. 10). Alternatively, the sampling device 56 may be directly connected to an intravenous catheter hub without additional components such as the extension tubing 57, to reduce the number of components and simplify the collection and sampling process.

The system 10d may further include a point-of-care testing device 58. Test strips, glass slides, and diagnostic cartridges are point-of-care testing devices 58 that receive a blood sample and test the blood for one or more physiological and biochemical states. Examples of testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers.

As is known in the art, the blood sampling device 56 may be disconnected from the extravascular fluid collection system as shown by arrow 210. The disconnected blood sampling device 56 is used to introduce a portion of the fluid sample to the point-of-care testing device 58, as shown by arrow 212. The fluid sample causes the point of care testing device 58 to change color or to undergo some other identifiable transformation to identify the presence or absence of certain analytes in the fluid sample, when read by and used with a testing instrument. In certain embodiments of the system 10d, the wearable electronic device 18 may be configured to capture an image of the used point-of-care testing device 58. The image processing functionality may be configured to read the point-of-care testing device 58 and determine test results. Alternatively, the image may be transmitted to a remote location, where it can be read or interpreted by an appropriate medical professional.

As in previous embodiments of the system 10*d*, the system 10*d* includes identification tags 30 attached to the various containers or blood sampling devices 56, invasive access devices, such as vascular access devices, and point-of-care testing devices 58. The identification tags 30 include or are associated with identifying information about the container or device. The identifying information may include the type of blood sampling device 56 or container, procedure the container or device is used for, or fluid volume of the sample obtained. The identifying information may also include a unique designation for each container, allowing the system 10*d* to track the container once a fluid sample is deposited therein. As in previously described aspects of the invention, the identification tags 30 can be any type of indicia, such as a barcode or QR code, that can be read by the image capture capabilities of the wearable electronic device 18. The identification tag 30 may also be an NFC tag, such as an RFID tag, that can be read by an antenna or transmitter associated with the wearable electronic device 18.

The system 10*d* may also include a patient ID 38, such as a wrist band 40 worn by the patient. The patient ID 38 includes an identification tag 30, such as a QR code, including or associated with patient information. The patient ID 38 allows the wearable electronic device 18 to access the patient's electronic information, such as patient information stored on an external patient database system. The wearable electronic device 18 is configured to receive the patient data and to display relevant information to the technician.

With reference to FIG. 6, the wearable electronic device 18 allows the technician to see a virtual layer 22 including a user interface 110. The user interface 110 is designed to provide relevant and important information to the technician in a manner which is easy to understand. An exemplary user interface 110 is illustrated in FIG. 6. It is understood, however, that the information, content, and design of the user interface 110 may be adapted for a particular type of medical facility or medical procedure. The appearance of the interface 110 may even be adapted based on the preferences of a particular technician.

The user interface 110 includes one or more information portions that display information about the patient, test being performed, containers being used, and other relevant data. For example, the user interface 110 may include a portion 118 with patient identifying information, such as a patient ID number. The patient information portion 118 may also include information about the type of sample ordered and a visual confirmation when the ordered sample is obtained. The user interface 110 may also include an identification tag portion, such as an identification tag confirmation icon 116. The identification tag confirmation icon 116 may include a visual indication when an identification tag 30 has been recognized and read correctly. The user interface 110 may also include a sample collection portion 120, showing an icon 122 of the sample collection container, such as a test tube. The icon 122 may change appearance when the sample is safely sealed in the container. In certain embodiments, the icon 122 may visually illustrate that the container is being filled with the fluid sample and may display a visual alert when a sufficient fluid volume has been obtained.

In use, the technician may begin by scanning the patient ID 38 by placing the patient ID 38 within the field of view 100 of the wearable electronic device 18, so that the patient information can be read by the wearable electronic device 18. Based on the patient information, details about the patient and test to be performed are displayed to the technician on the user interface 110. The technician may then collect the blood sampling device 56 and other items needed for the particular procedure to be performed. In certain embodiments, the wearable electronic device 18 may recognize each item as it is obtained by the technician by, for example, recognizing and reading an identification tag 30 affixed to the item. The user interface 110 may inform the technician after each required item is acquired. The user interface 110 may also display an alert if a required item has not yet been acquired or recognized.

The user interface 110 may then display instructions for obtaining the fluid sample. These instructions may include the fluid volume required, suggested vascular access sites, or any other relevant information. The technician then collects the sample into the blood sampling device 56 or another suitable container. The image capture feature of the wearable electronic device 18 may capture images of the sampling device 56 or container being filled by the sample and may alert the technician when a sufficient fluid volume is obtained. Once the sample is obtained, the technician may seal the sampling device 56 or container. The image capture functionality of the wearable electronic device 18 may document that the sample has been obtained and record the time and a unique identification number for the sampling device 56 or container. In this way, the container is electronically tied to the particular patient and the possibility that a sample will be lost or identified with the wrong patient is reduced.

If point-of-care testing is to be performed, details about performing the test may be presented to the technician. The technician prepares the testing device 58 by, for example, placing it on a table or other suitable surface. Preferably, the surface is white or a similar high-contrast color to improve the quality of an image of the testing device 58 taken by the wearable electronic device 18. The identification tag 30 of the testing device 58 is identified and recorded by the image capture functionality. The technician may then perform the test by, for example, placing a drop of the fluid sample on the testing device 58. The system 10*d* may wait a predetermined period of time for the test to be performed and then obtain an image of the used testing device 58. The captured image may be processed to determine test results. Alternatively, the technician may visually determine test results and record the information using data input functionality of the wearable electronic device 18. If the testing device 58 must be preserved and sent to a laboratory or other facility, then the image capture functionality may record the identification tag 30 and identification information about the specific testing device 58 used to ensure correct chain of custody. As in previous embodiments of the system 10, the wearable electronic device 18 monitors each step of the sample acquisition and testing process. If the technician misses a step, the user interface 110 would alert the technician and provide instructions for correcting any mistakes.

Figure 8:
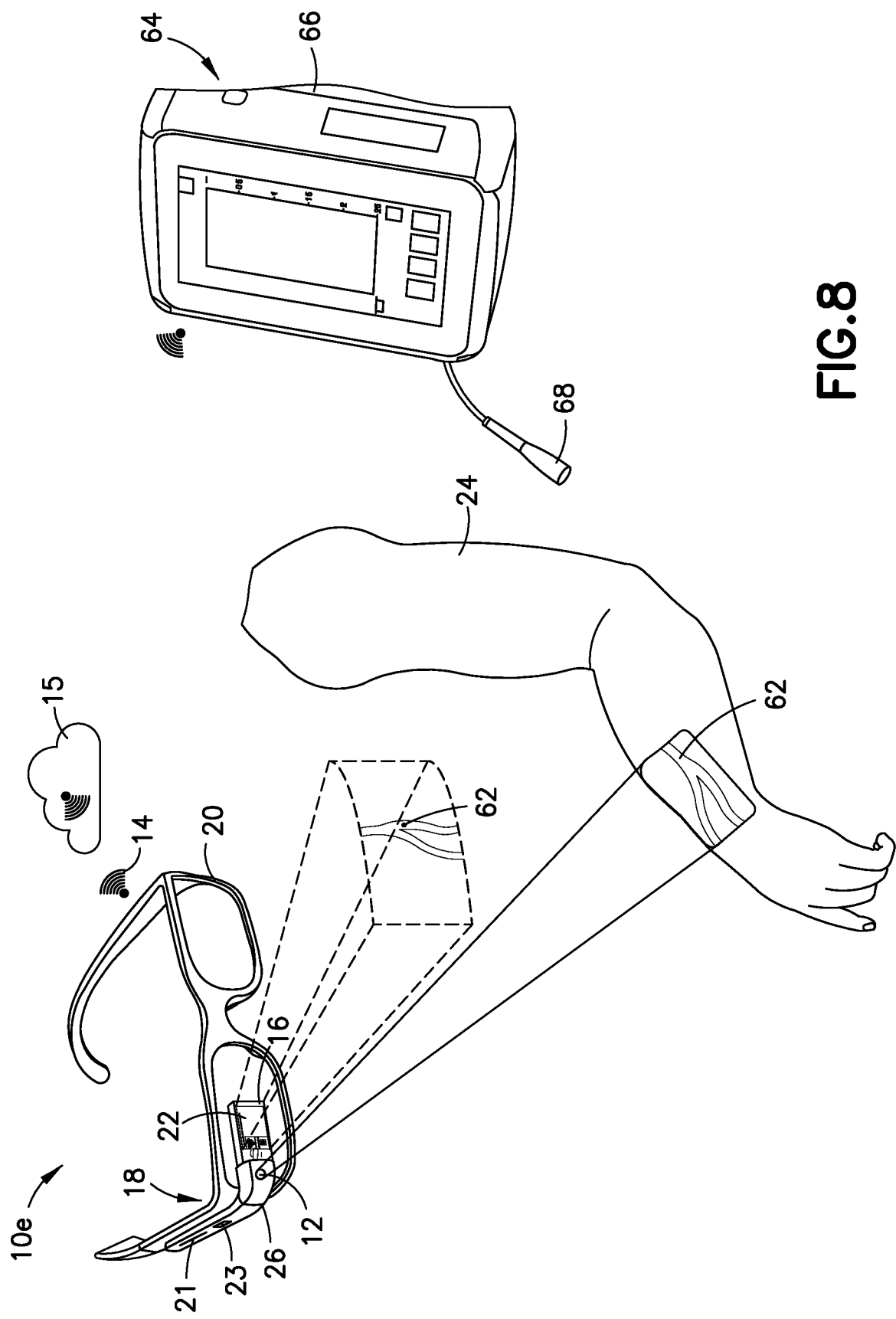
FIG. 8 is a schematic representation of a system for enhanced visualization during insertion of the invasive device, according to the principles of the invention.
Figure 9:
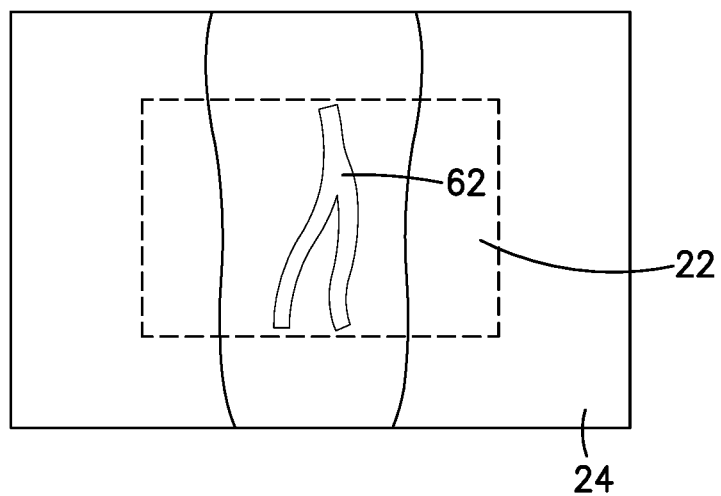
FIG. 9 is a schematic representation of a field of view for the system of FIG. 8.
Figure 10:
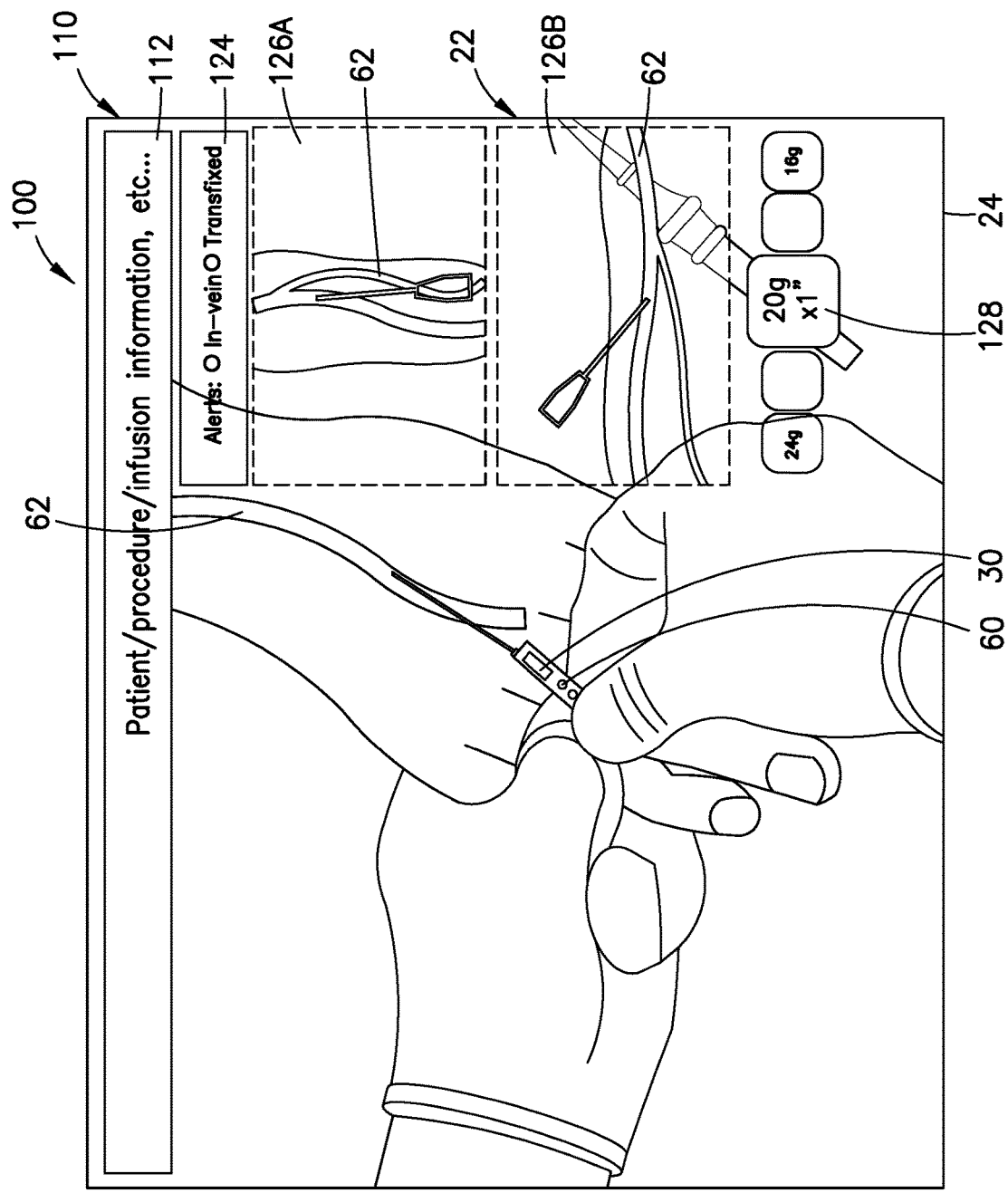
FIG. 10 is a schematic representation of a field of view for the system of FIG. 9.

According to another aspect of the invention and with reference to FIGS. 7-10, a system 10*e* for enhanced visualization during insertion of an invasive access device, such as vascular access device 60, and assessment of an indwelling vascular access device 60 is illustrated. The vascular access device 60 may be any suitable device for injecting or acquiring a fluid sample from a vein, including, but not limited to, a syringe, hypodermic needle, peripheral intravenous catheter, blood collection set, central line, or any combinations of these elements. Exemplary vascular access devices 60 include straight and ported intravenous catheters such as the AUTOGUARD™ shielded catheter by Becton, Dickinson and Company, integrated peripheral intravenous catheters, winged needle sets, and blood collection sets. An exemplary catheter for use with the system is depicted in FIG. 10. As in previously described embodiments, the system 10e may be integrated with a patient data system for identifying a medical procedure to be performed and for treatment confirmation.

The system 10e includes a wearable electronic device 18 described in detail above. The system 10e further includes the vascular access device 60. The vascular access device 60 may include one or more identification tags 30 including or associated with information about the vascular access device 60. The information may include the needle gauge and length, as well as other relevant information required for a particular procedure, including but not limited to patient information, time, date, and other patient or procedure specific parameters. The system 10e may further include a patient ID 38 (shown on FIG. 3) worn by the patient. The patient ID 38 allows the system 10e to automatically identify the patient and may be linked to the patient's electronic record.

In certain embodiments, the wearable electronic device 18 also includes or is associated with additional systems, such as ultrasonic or other scanning devices which externally or internally enhance anatomical structures. This enhanced anatomical structures may assist the technician in positioning the vascular access device 60 by providing a visual indication (e.g., a virtual trace 62) of the location of a vein suitable for needle insertion. The technician can orient the needle of the vascular access device 60 based on the position of the virtual trace 62.

In certain embodiments, the virtual trace 62 is projected to the field of view 100 of the technician using the display functionality of the wearable electronic device 18. The virtual trace 62 may be a computer-generated image or icon indicating where a vein is present. The position of the vein may be determined by a number of different image processing techniques. In one embodiment of the system 10e, an image of the injection site is captured by the image capture functionality of the wearable electronic device 18. Image processing performed on the captured image identifies various anatomical markers on the image. For example, the anatomic position of portions of the arm (e.g., wrist, elbow, fingers, etc.) may be identified. In an alternative embodiment, anatomical markers may be placed directly on the exterior of the patient's skin or applied to a dressing. Based on the location of these anatomical markers, distance between the markers, and orientation of the arm relative to the image capture functionality, the size and shape of the arm can be calculated. Once the position and size of the arm is identified, approximate vein position can be estimated. The virtual trace 62, based on these estimates, is projected to the field of view 100 of the technician in the approximated position. The virtual trace 62 is viewable over the reality layer 24 of the field of view 100, including the patient's arm.

With reference to FIG. 8, in certain embodiments, the visualization based on anatomical positioning is enhanced based on readings obtained using various external imaging devices, such as ultrasound, infrared imaging, magnetic resonance imaging (MRI), or combinations thereof. As shown in FIG. 8, the system 10e is provided with an external ultrasound monitor 64 comprising a control module 66 and attached to a wand 68 or scanner. The control module 66 may include an integrated display. The ultrasound monitor 64 may be used to obtain an initial image of the patient's vascular anatomy prior to performing the invasive procedure. The ultrasound image obtained may be helpful for automatically differentiating between arteries and veins, may help to determine which vein is most suitable for a particular vascular access, and may assist in selecting a correct catheter size and length for a particular vein. The image of the injection site captured by the digital camera 12 may be captured simultaneously with obtaining an ultrasound scan to facilitate lining up the two images.

Once the images are obtained and a desirable invasive access site and vein is determined, this location information is transmitted to the wearable electronic device 18 and used in conjunction with the anatomic positioning information obtained by processing the captured image to determine the location for the virtual trace 62. The approximate location of the preferred vein and injection site is projected into the field of view 100 (shown on FIG. 10) of the technician. The virtual vein trace 62 could be color-coded or animated to provide additional information to the technician. For example, vein diameter information could be projected next to each virtual vein trace 62, to assist the technician in selecting a vein of an appropriate size and to assist in selecting an appropriately sized catheter. Similarly, veins of different sizes could be displayed in different colors to assist in the selection process.

Integrating data obtained by an imaging device, such as ultrasound, improves selectivity, accuracy, and specificity of the external visualization information projected to the technician. Accordingly, the technician can trust that the vein location being displayed is correct and is a vein suitable in size for the type of vascular access device 60 being used.

The ultrasound image of vein anatomy can be saved locally on the wearable electronic device 18 or transmitted to an external data device, such as a patient database system, for inclusion in the patient's record. The ultrasound image could then be automatically provided for subsequent vascular access treatments to assist in vein selection.

After the insertion is performed, the system 10e may be configured to obtain a real-time ultrasound image to confirm correct placement of the needle of the vascular access device 60 in the vein. Similarly, the system 10e could record a time and date stamp for the insertion and include such information in the patient's record. The system 10e may also record the location of the vascular insertion. This information may be used to prevent repeat insertion in the same area of the patient's body.

In certain further embodiments, the ultrasound monitor 64 may be configured to provide real-time information to the technician. For example, the user interface 110 of the wearable electronic device 18 may be configured to provide a real-time image obtained with the ultrasound monitor 64 to the technician's field of view 100. In this way, the technician could "watch" the insertion process to ensure that the vascular access device 60 is correctly inserted into the desired vein. Such real-time information allows the technician to correct for changes to anatomical structure and device location, which may occur during the insertion process. Similarly, such a real-time system could be useful for assessing the viability, location, and changes in vein structure of an indwelling vascular access device 60. Thus, the technician would be better able to determine when an indwelling vascular access device 60 needs to be removed or repositioned.

In a further embodiment, the wearable electronic device 18 may include means for sub-dermal illumination by projecting light or radiation, such as light provided by one or more LED bulbs or laser lightpipes onto the patient's skin. The projected light may enhance visualization of the veins and could be used to improve the quality of the captured image. The enhanced captured image could be used to improve the approximated virtual trace 62 provided by the image processing functionality. Inter-cannula illumination or illumination with catheter stripes may also be used for increasing actual visualization of arteries and veins within the scope of the present invention.

The invasive device of the system may also be composed of a material that may be magnetized for use with ultrasonic systems that utilize a magnetic feature to enhance visualization and provide a means of projection in the form of a path as the invasive device moves toward the targeted anatomy.

As in previously described systems 10*e*, the user interface 110 projected to the virtual layer 22 of the technician's field of view 100 is beneficial for conveying important information about the procedure to be performed, devices being used, and progress of the insertion process to the technician in a convenient and hands-free manner. With reference to FIG. 8, the overall user visual experience of the system 10*e* includes having a virtual layer 22 projected over the technician's field of view 100 (shown in FIG. 10) that highlights the patient's vascular anatomy, giving the technician improved insertion success. FIG. 9 is a schematic representation of a virtual vein trace 62 covering a portion of a patient's arm.

With reference to FIG. 10, a further embodiment of the technician's field of view 100 including a virtual layer 22 projected over a reality layer 24 is depicted. The virtual layer 22 includes a user interface 110 consisting of a heading bar 112, which includes patient identifying information and information about the procedure to be performed. The user interface 110 also includes an alert portion 124 that shows the technician when the needle of the vascular access device 60 is in the vein or when the needle has been transfixed, and the projected trajectory of the invasive device while it is being placed relative to the targeted sub-dermal anatomy. The user interface 110 also includes one or more schematic images 126 showing the position of the needle relative to the vein. For example, one schematic image 126A may show the position of the needle relative to the vein from a top view, to show the technician whether the needle must be moved left or right, forward or backward. The user interface 110 may also include a second schematic image 126B depicting an elevation or side view, showing the depth of the needle relative to the vein. It is further contemplated herein that additional schematic drawings depicting other images or views of the desired structures may be provided for view in the user interface 110. For example, other views may include a cross-sectional view of the images shown in first schematic image 126A or the second schematic image 126B. Alternatively, an image taken out of the plane, such as an ultra sound probe, may also be provided. Finally, the user interface 110 may include icons 128 showing certain information about the vascular access device 60, such as the gauge or length of the catheter or needle.

In use, the technician begins by determining what procedure should be performed and obtaining necessary equipment. As in previous embodiments of the system 10*e*, the technician may determine this information by scanning the patient ID 38. Based on the information obtained from the patient ID 38, the user interface 110 may display instructions for the procedure to be performed, instructions for what items must be obtained, and any other relevant information concerning the procedure or patient. The technician then obtains the items for the procedure, namely the vascular access device 60. The system 10*e* may verify that the correct items have been obtained by scanning an identification tag 30 for each item. An alert may display if the technician has failed to obtain a needed item.

Prior to performing the injection or vascular access procedure, the technician may scan the desired insertion site with the wand 68 or scanner of the imaging device, such as the ultrasound monitor 64, to obtain a sub-dermal three-dimensional image of the patient's vasculature. The system 10*e* may automatically process the obtained images and identify a suitable vein for insertion of the vascular access device 60. While the vein is being identified, an image of the injection site is also obtained using the image capture functionality, such as the digital camera 12 of the wearable electronic device 18. Processing the captured image identifies various anatomical markers, which are used to determine the size, shape, and orientation of the patient's arm or other chosen injection site. Based on these processing activities, a trace of the vein, referred to herein as the virtual vein trace 62, is shown to the technician on the user interface 110. The technician positions the needle of the vascular access device 60 based on the virtual trace 62. The technician then inserts the needle into the vein. The user interface 110 may display an alert or confirmation when the needle is positioned correctly.

In addition to assisting in the positioning of the needle, the system 10*e* documents the insertion activities to confirm that the procedure was in fact carried out correctly. For example, the time of the insertion, insertion location, name of the technician, insertion site, and other information may be transmitted from the wearable electronic device 18 to a patient data system. The information is recorded to assist in performing future insertion procedures.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof. Further, although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system comprising:
   a wearable electronic device configured to be worn by a user comprising:
   a housing,
   at least one imaging sensor associated with the housing,
   a data transmission interface for sending data to or receiving the data from an external electronic device,
   a data reporting accessory for providing the data to the user,
   a microprocessor for managing the at least one imaging sensor, the data transmission interface, and the data reporting accessory, and
   a program for acquiring and processing images from the at least one imaging sensor;

a fluid delivery apparatus for passively or actively delivering a therapeutic agent to a patient; and
one or more identification tags attached to or integrally formed with the fluid delivery apparatus,
wherein the program processes a series of images captured by the at least one imaging sensor to identify the one or more identification tags and acquire fluid delivery apparatus information from the one or more identification tags,
wherein the wearable electronic device is a head-worn computer, and wherein the data reporting accessory is a projection prism configured to project a virtual layer to a field of view of the user,
wherein the virtual layer includes a virtual trace projected to the field of view of the user, wherein the virtual trace comprises a computer-generated image or icon indicating a location of a vein of the patient in the field of view of the user, and
wherein the program determines one or more anatomical markers in the series of images, estimates a position of the vein of the patient in the series of images based on the one or more anatomical markers, and projects the virtual trace including the computer-generated image or icon indicating the location of the vein of the patient in the field of view of the user based on the estimated position of the vein of the patient in the series of images.

2. The system of claim 1, further comprising:
an ultrasound imaging device that obtains at least one ultrasound image of the patient, wherein the program processes the series of images captured by the at least one imaging sensor in conjunction with the at least one ultrasound image to determine the location of the vein of the patient in the field of view of the user.

3. The system of claim 1, wherein the one or more anatomical markers include at least one anatomic position of a portion of an arm of the patient and at least one anatomical marker placed directly on the exterior of the skin of the patient or applied to a dressing of the patient.

4. A system comprising:
a wearable electronic device configured to be worn by a user comprising:
a housing,
at least one imaging sensor associated with the housing,
a data transmission interface for sending data to or receiving the data from an external electronic device,
a data reporting accessory for providing the data to the user,
a microprocessor for managing the at least one imaging sensor, the data transmission interface, and the data reporting accessory, and
a program for acquiring and processing images from the at least one imaging sensor;
a fluid delivery apparatus for passively or actively delivering a therapeutic agent to a patient; and
one or more identification tags attached to or integrally formed with the fluid delivery apparatus,
wherein the program processes a series of images captured by the at least one imaging sensor to identify the one or more identification tags and acquire fluid delivery apparatus information from the one or more identification tags,
wherein the wearable electronic device is a head-worn computer, and wherein the data reporting accessory is a projection prism configured to project a virtual layer to a field of view of the user,
wherein the virtual layer includes a virtual trace projected to the field of view of the user, wherein the virtual trace comprises a computer-generated image or icon indicating a location of a vein of the patient in the field of view of the user, and
wherein the virtual layer includes an indication of a diameter of the vein projected next to the virtual trace comprising the computer-generated image or icon indicating the location of the vein.

5. A system comprising:
a wearable electronic device configured to be worn by a user comprising:
a housing,
at least one imaging sensor associated with the housing,
a data transmission interface for sending data to or receiving the data from an external electronic device,
a data reporting accessory for providing the data to the user,
a microprocessor for managing the at least one imaging sensor, the data transmission interface, and the data reporting accessory, and
a program for acquiring and processing images from the at least one imaging sensor;
a fluid delivery apparatus for passively or actively delivering a therapeutic agent to a patient; and
one or more identification tags attached to or integrally formed with the fluid delivery apparatus,
wherein the program processes a series of images captured by the at least one imaging sensor to identify the one or more identification tags and acquire fluid delivery apparatus information from the one or more identification tags,
wherein the wearable electronic device is a head-worn computer, and wherein the data reporting accessory is a projection prism configured to project a virtual layer to a field of view of the user,
wherein the virtual layer includes a virtual trace projected to the field of view of the user, wherein the virtual trace comprises a computer-generated image or icon indicating a location of a vein of the patient in the field of view of the user, and
wherein the virtual trace comprises a plurality of virtual traces, wherein the computer-generated image or icon includes a plurality of computer-generated images or icons, wherein the vein of the patient includes a plurality of veins of the patient, wherein the virtual layer comprises the plurality of virtual traces comprising the plurality of computer-generated images or icons indicating locations of the plurality of veins of the patient in the field of view of the user, and wherein the plurality of veins are displayed in different colors in the virtual layer to indicate different diameters of the plurality of veins.

6. A system comprising:
a wearable electronic device configured to be worn by a user comprising:
a housing,
at least one imaging sensor associated with the housing,
a data transmission interface for sending data to or receiving the data from an external electronic device,
a data reporting accessory for providing the data to the user,
a microprocessor for managing the at least one imaging sensor, the data transmission interface, and the data reporting accessory, and
a program for acquiring and processing images from the at least one imaging sensor;

a fluid delivery apparatus for passively or actively delivering a therapeutic agent to a patient; and one or more identification tags attached to or integrally formed with the fluid delivery apparatus, wherein the program processes a series of images captured by the at least one imaging sensor to identify the one or more identification tags and acquire fluid delivery apparatus information from the one or more identification tags, wherein the wearable electronic device is a head-worn computer, and wherein the data reporting accessory is a projection prism configured to project a virtual layer to a field of view of the user, wherein the virtual layer includes a virtual trace projected to the field of view of the user, wherein the virtual trace comprises a computer-generated image or icon indicating a location of a vein of the patient in the field of view of the user, and wherein the virtual layer comprises (i) a heading bar including information about a procedure to be performed determined based on the fluid delivery apparatus information from the one or more identification tags and (ii) an alert portion that shows when a needle of the fluid delivery apparatus is transfixed in the vein of the patient and a projected trajectory of the needle when the needle is being placed relative to the vein.

7. The system of claim 6, wherein the information about the procedure to be performed includes a gauge and length of the needle of the fluid delivery apparatus.

8. A system comprising:
a wearable electronic device configured to be worn by a user comprising:
a housing,
at least one imaging sensor associated with the housing,
a data transmission interface for sending data to or receiving the data from an external electronic device,
a data reporting accessory for providing the data to the user,
a microprocessor for managing the at least one imaging sensor, the data transmission interface, and the data reporting accessory, and
a program for acquiring and processing images from the at least one imaging sensor;
a fluid delivery apparatus for passively or actively delivering a therapeutic agent to a patient; and
one or more identification tags attached to or integrally formed with the fluid delivery apparatus,
wherein the program processes a series of images captured by the at least one imaging sensor to identify the one or more identification tags and acquire fluid delivery apparatus information from the one or more identification tags,
wherein the wearable electronic device is a head-worn computer, and wherein the data reporting accessory is a projection prism configured to project a virtual layer to a field of view of the user,
wherein the virtual layer includes a virtual trace projected to the field of view of the user, wherein the virtual trace comprises a computer-generated image or icon indicating a location of a vein of the patient in the field of view of the user, and
wherein the virtual layer comprises (i) a first schematic image that shows a position of a needle of the fluid delivery apparatus relative to the vein from a top view, (ii) a second schematic image that shows a depth of the needle relative to the vein from an elevation or side view different than the top view, and (iii) a cross-sectional view of the first schematic image or the second schematic image.

9. A system comprising:
a wearable electronic device configured to be worn by a user comprising:
a housing,
at least one imaging sensor associated with the housing,
a data transmission interface for sending data to or receiving the data from an external electronic device,
a data reporting accessory for providing the data to the user,
a microprocessor for managing the at least one imaging sensor, the data transmission interface, and the data reporting accessory, and
a program for acquiring and processing images from the at least one imaging sensor;
a fluid delivery apparatus for passively or actively delivering a therapeutic agent to a patient; and
one or more identification tags attached to or integrally formed with the fluid delivery apparatus,
wherein the program processes a series of images captured by the at least one imaging sensor to identify the one or more identification tags and acquire fluid delivery apparatus information from the one or more identification tags,
wherein the wearable electronic device is a head-worn computer, and wherein the data reporting accessory is a projection prism configured to project a virtual layer to a field of view of the user,
wherein the virtual layer includes a virtual trace projected to the field of view of the user, wherein the virtual trace comprises a computer-generated image or icon indicating a location of a vein of the patient in the field of view of the user, and
wherein the fluid delivery apparatus comprises an infusion set, and wherein the program is configured to process the series of images to visually monitor a drip count of the infusion set, and wherein the program determines an amount of fluid delivered to the patient over a period of time based on the drip count.

10. A method comprising:
capturing, with at least one imaging sensor associated with a housing of a wearable electronic device worn by a user, a series of images, wherein the wearable electronic device is a head-worn computer comprising a projection prism;
processing, with at least one processor, the series of images captured by the at least one imaging sensor to identify one or more identification tags attached to or integrally formed with a fluid delivery apparatus and acquire fluid delivery apparatus information from the one or more identification tags;
projecting, with the projection prism, a virtual layer to a field of view of the user, wherein the virtual layer includes a virtual trace projected to the field of view of the user, and wherein the virtual trace comprises a computer-generated image or icon indicating a location of a vein of a patient in the field of view of the user;
determining, with the at least one processor, one or more anatomical markers in the series of images;
estimating, with the at least one processor, a position of the vein of the patient in the series of images based on the one or more anatomical markers; and
projecting, with the projection prism, the virtual trace including the computer-generated image or icon indicating the location of the vein of the patient in the field of view of the user based on the estimated position of the vein of the patient in the series of images.

11. The method of claim 10, further comprising:
obtaining, with an ultrasound imaging device, at least one ultrasound image of the patient; and
processing, with the at least one processor, the series of images captured by the at least one imaging sensor in conjunction with the at least one ultrasound image to determine the location of the vein of the patient in the field of view of the user.

12. The method of claim 10, wherein the one or more anatomical markers include at least one anatomic position of a portion of an arm of the patient and at least one anatomical marker placed directly on the exterior of the skin of the patient or applied to a dressing of the patient.

13. A method comprising:
capturing, with at least one imaging sensor associated with a housing of a wearable electronic device worn by a user, a series of images, wherein the wearable electronic device is a head-worn computer comprising a projection prism;
processing, with at least one processor, the series of images captured by the at least one imaging sensor to identify one or more identification tags attached to or integrally formed with a fluid delivery apparatus and acquire fluid delivery apparatus information from the one or more identification tags; and
projecting, with the projection prism, a virtual layer to a field of view of the user, wherein the virtual layer includes a virtual trace projected to the field of view of the user, and wherein the virtual trace comprises a computer-generated image or icon indicating a location of a vein of a patient in the field of view of the user,
wherein the virtual layer includes an indication of a diameter of the vein projected next to the virtual trace comprising the computer-generated image or icon indicating the location of the vein.

14. A method comprising:
capturing, with at least one imaging sensor associated with a housing of a wearable electronic device worn by a user, a series of images, wherein the wearable electronic device is a head-worn computer comprising a projection prism;
processing, with at least one processor, the series of images captured by the at least one imaging sensor to identify one or more identification tags attached to or integrally formed with a fluid delivery apparatus and acquire fluid delivery apparatus information from the one or more identification tags; and
projecting, with the projection prism, a virtual layer to a field of view of the user, wherein the virtual layer includes a virtual trace projected to the field of view of the user, and wherein the virtual trace comprises a computer-generated image or icon indicating a location of a vein of a patient in the field of view of the user,
wherein the virtual trace comprises a plurality of virtual traces, wherein the computer-generated image or icon includes a plurality of computer-generated images or icons, wherein the vein of the patient includes a plurality of veins of the patient, wherein the virtual layer comprises the plurality of virtual traces comprising the plurality of computer-generated images or icons indicating locations of the plurality of veins of the patient in the field of view of the user, and wherein the plurality of veins are displayed in different colors in the virtual layer to indicate different diameters of the plurality of veins.

15. A method comprising:
capturing, with at least one imaging sensor associated with a housing of a wearable electronic device worn by a user, a series of images, wherein the wearable electronic device is a head-worn computer comprising a projection prism;
processing, with at least one processor, the series of images captured by the at least one imaging sensor to identify one or more identification tags attached to or integrally formed with a fluid delivery apparatus and acquire fluid delivery apparatus information from the one or more identification tags; and
projecting, with the projection prism, a virtual layer to a field of view of the user, wherein the virtual layer includes a virtual trace projected to the field of view of the user, and wherein the virtual trace comprises a computer-generated image or icon indicating a location of a vein of a patient in the field of view of the user,
wherein the virtual layer comprises (i) a heading bar including information about a procedure to be performed determined based on the fluid delivery apparatus information from the one or more identification tags and (ii) an alert portion that shows when a needle of the fluid delivery apparatus is transfixed in the vein of the patient and a projected trajectory of the needle when the needle is being placed relative to the vein.

16. The method of claim 15, wherein the information about the procedure to be performed includes a gauge and length of the needle of the fluid delivery apparatus.

17. A method comprising:
capturing, with at least one imaging sensor associated with a housing of a wearable electronic device worn by a user, a series of images, wherein the wearable electronic device is a head-worn computer comprising a projection prism;
processing, with at least one processor, the series of images captured by the at least one imaging sensor to identify one or more identification tags attached to or integrally formed with a fluid delivery apparatus and acquire fluid delivery apparatus information from the one or more identification tags; and
projecting, with the projection prism, a virtual layer to a field of view of the user, wherein the virtual layer includes a virtual trace projected to the field of view of the user, and wherein the virtual trace comprises a computer-generated image or icon indicating a location of a vein of a patient in the field of view of the user,
wherein the virtual layer comprises (i) a first schematic image that shows a position of a needle of the fluid delivery apparatus relative to the vein from a top view, (ii) a second schematic image that shows a depth of the needle relative to the vein from an elevation or side view different than the top view, and (iii) a cross-sectional view of the first schematic image or the second schematic image.

18. A method comprising:
capturing, with at least one imaging sensor associated with a housing of a wearable electronic device worn by a user, a series of images, wherein the wearable electronic device is a head-worn computer comprising a projection prism;
processing, with at least one processor, the series of images captured by the at least one imaging sensor to identify one or more identification tags attached to or integrally formed with a fluid delivery apparatus and acquire fluid delivery apparatus information from the one or more identification tags; and projecting, with the projection prism, a virtual layer to a field of view of the user, wherein the virtual layer includes a virtual trace projected to the field of view of the user, and wherein the virtual trace comprises a computer-generated image or icon indicating a location of a vein of a patient in the field of view of the user, wherein the fluid delivery apparatus comprises an infusion set, the method further comprising:

processing, with the at least one processor, the series of images to visually monitor a drip count of the infusion set; and determining, with the at least one processor, an amount of fluid delivered to the patient over a period of time based on the drip count.

\* \* \* \* \*